US008178649B2

(12) United States Patent
Eggink et al.

(10) Patent No.: US 8,178,649 B2
(45) Date of Patent: May 15, 2012

(54) IMMUNOSTIMULATORY COMPOSITIONS AND USES THEREOF

(75) Inventors: Laura Eggink, Scottsdale, AZ (US);
Valerie Jacobs, Phoenix, AZ (US);
Srilakshmi Bysani, Phoenix, AZ (US);
Kenneth J. Hoober, Phoenix, AZ (US)

(73) Assignee: Arizona Biomedical Research Commission, Phoenix, AZ (US)

( * ) Notice: Subject to any disclaimer, the term of this patent is extended or adjusted under 35 U.S.C. 154(b) by 198 days.

(21) Appl. No.: 11/663,899

(22) PCT Filed: Dec. 6, 2005

(86) PCT No.: PCT/US2005/044215
§ 371 (c)(1),
(2), (4) Date: Nov. 14, 2007

(87) PCT Pub. No.: WO2006/063028
PCT Pub. Date: Jun. 15, 2006

(65) Prior Publication Data
US 2008/0102076 A1    May 1, 2008

Related U.S. Application Data

(60) Provisional application No. 60/633,825, filed on Dec. 7, 2004.

(51) Int. Cl.
*C07K 2/00* (2006.01)
*A61K 38/00* (2006.01)
(52) U.S. Cl. .......................................... 530/300; 514/2
(58) Field of Classification Search ........................ None
See application file for complete search history.

(56) References Cited

U.S. PATENT DOCUMENTS

| 5,641,747 | A | 6/1997 | Popoff et al. |
|---|---|---|---|
| 5,677,276 | A | 10/1997 | Dickerson et al. |
| 5,753,481 | A | 5/1998 | Niwa et al. |
| 5,910,310 | A | 6/1999 | Heinen et al. |
| 5,919,998 | A | 7/1999 | Bandurski et al. |
| 6,159,937 | A | 12/2000 | Larsen et al. |
| 6,193,981 | B1 | 2/2001 | Goldstein |
| 6,498,020 | B1 | 12/2002 | Walker et al. |
| 6,551,795 | B1 | 4/2003 | Rubenfield et al. |
| 7,105,481 | B2 | 9/2006 | Uutela et al. |
| 2003/0073637 | A1 | 4/2003 | Uutela et al. |
| 2004/0031072 | A1 | 2/2004 | La Rosa et al. |
| 2004/0123343 | A1 | 6/2004 | La Rosa et al. |
| 2004/0248192 | A1 | 12/2004 | Marchalonis et al. |
| 2005/0063937 | A1 | 3/2005 | Li et al. |
| 2006/0024668 | A1 | 2/2006 | Hock |
| 2006/0078535 | A1 | 4/2006 | Livant |
| 2006/0148093 | A1* | 7/2006 | Gygi et al. ................ 436/173 |
| 2006/0160730 | A1 | 7/2006 | Cuttitta et al. |
| 2006/0189538 | A1 | 8/2006 | Secombes et al. |
| 2006/0269519 | A1 | 11/2006 | Chen et al. |
| 2006/0287234 | A1 | 12/2006 | Breen et al. |
| 2007/0003542 | A1 | 1/2007 | Zimmerman et al. |
| 2007/0021342 | A1 | 1/2007 | Breen et al. |
| 2007/0149475 | A1 | 6/2007 | Murray et al. |
| 2007/0154448 | A1 | 7/2007 | Reid et al. |
| 2008/0102076 | A1 | 5/2008 | Eggink et al. |
| 2009/0041793 | A1 | 2/2009 | Eggink et al. |

FOREIGN PATENT DOCUMENTS

| CA | 2290722 | 6/2001 |
|---|---|---|
| WO | WO 96/40903 | 12/1996 |
| WO | 00/31130 | 6/2000 |
| WO | WO 02/058589 | 8/2002 |
| WO | 03/091275 | 11/2003 |
| WO | WO 2004/011650 | 2/2004 |
| WO | 2005/087793 | 9/2005 |
| WO | 2006/063028 | 6/2006 |
| WO | 2006-105021 | 10/2006 |

OTHER PUBLICATIONS

Sigma chemical company catalog, p. 632, 1996.*
European Search Report for European patent application No. 07869233.2 dated May 11, 2010.
Glaxosmithkline, (2005a) Study of Chemokine Coreceptor 5 (CCR5) Antagonist GW873140 in R5-Tropic Treatment-Experienced HIV Infected Subjects, ClinicalTrials.gov (Sep. 13, 2005) Identifier: NCT00197145S, (Terminated in 2005).
Glaxosmithkline, (2005b) "GlaxoSmithKline Halts Trials of Experimental CCR5 Inhibitor Aplaviroc in Treatnnentnaïve HIV Patients Due to Concerns about Liver Toxicity," Statement of HIV Patient Community: Information from GlaxoSmithKline on Changes to Studies Investigational CCR5 Entry Inhibitor Aplaviroc (GW873140) (Sep. 15, 2005), pp. 1-2.
International Search Report for WO/2006/063028 dated Nov. 16, 2006 (6 sheets).
International Search Report for WO/2005/087793 dated Apr. 5, 2006 (6 sheets).
PCT/US2007/087413 International Search Report dated Jul. 29, 2008.
PCT/US2007/087425 International Search Report dated Aug. 5, 2008.
Supplementary European Search Report for European application No. 07871699.0 dated May 17, 2010 (8 sheets).
Written Opinion of the International Searching Authority for WO/2005/087793 dated Apr. 5, 2006 (7 sheets).
Written Opinion of the International Searching Authority for WO/2006/063028 dated Nov. 16, 2006 (9 sheets).
Written Opinion of the International Searching Authority for WO/2008/076815 dated Jul. 29, 2008 (6 sheets).
Written Opinion of the International Searching Authority for WO/2008/076824 dated Aug. 5, 2008 (6 sheets).
Chargelegue et al., "A Peptide Mimic of a Protective Epitope of Respiratory Syncytial Virus Selected from a Combinatorial Library Induces Virus-Neutralizing Antibodies and Reduces Viral Load in Vivo", Journal of Virology, 72 (3):2040-2046 (Mar. 1998).
Chersi et al., "Specifications of rabbit antisera to multiple antigen (MAP) peptides", ournal of Biosciences, 50 (9-10):735-738 (Sep. 1, 1995) Abstract Only.
Ciesielski et al., "Cellular antitumor immune response to a branched lysine multiple antigenic peptide containing epitopes of a common tumor-specific antigen in a rat giloma model", Cancer Immunol Immunother, 54:107-119 (2005).

(Continued)

Primary Examiner — Yunsoo Kim
(74) Attorney, Agent, or Firm — Banner & Witcoff, Ltd.

(57) ABSTRACT

The present invention provides novel immuno-stimulatory polypeptides, and methods for their use and identification.

13 Claims, 1 Drawing Sheet

OTHER PUBLICATIONS

Eggink et al., "A biologically active peptide mimetic of N-acetylgalactosamine/galactose", BMC Research Notes, 2:23 (2009).

G.Fätkenheuer et al., "Efficacy of Short-Term Monotherapy with Maraviroc, a New CRC5 Antagonist, in Patients Infected with HIV 1," Natire Med (2005), vol. 11, pp. 1170-1172.

J. Cohen, "Hope on New AIDS Drugs, but Breast-Feeding Strategy Backfires," Science (2007), vol. 315, pp. 1357.

J. Stover et al., "The Global Impact of Scaling up HIV/AIDS Prevention Programs in Low-and Middle-Income Countries," Science (2006) vol. 311, pp. 1474-1476.

Manki et al., "Vaccination with Multiple Antigen Peptide as Rejection Antigen Peptide in Murine Leukemia", Cancer Research, 58:1960-1964 (May 1, 1998).

Nicolaus, "Symbiotic Approach to Drug Design", Decision Making in Drug Reasearch, pp. 173-186 (Jan. 1, 1983).

Olszewska et al., "Protection against Measles Virus-Induced Encephalitis by Anti-mimotope Anitbodies: The Role of Antibody Affinity" Virology, 272(1):98-105 (Jun. 20, 2000).

P.W. Latham, "Therapeutic Peptides Revisited," Nature Biotech (1999), vol. 17, pp. 755-757.

Sarig, et al.; "Telomeric and Tetraplex DNA Binding Properties of qTBP42: A Homologue of the CArG Box Binding Protein CBF-A"; Biochemical and Biophysical Research Communications 1997, vol. 237, No. 3, pp. 617-623.

* cited by examiner

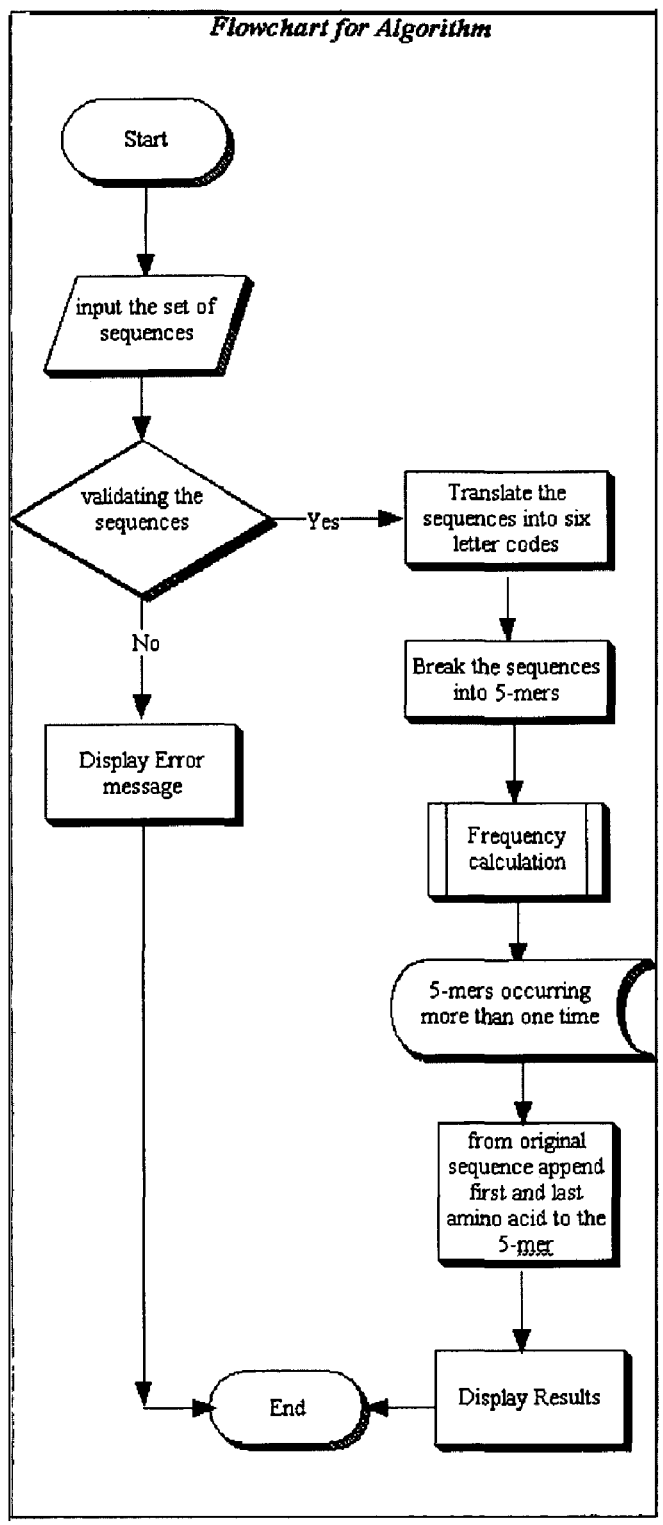

SEQUENCE LISTING

<160> NUMBER OF SEQ ID NOS: 152

<210> SEQ ID NO 1
<211> LENGTH: 9
<212> TYPE: PRT
<213> ORGANISM: Artificial
<220> FEATURE:
<223> OTHER INFORMATION: synthetic peptide

<400> SEQUENCE: 1

Cys Asn Ser Thr Thr Pro Ala Ser Cys
1               5

<210> SEQ ID NO 2
<211> LENGTH: 9
<212> TYPE: PRT
<213> ORGANISM: Artificial
<220> FEATURE:
<223> OTHER INFORMATION: synthetic peptide

<400> SEQUENCE: 2

Cys Asp Pro Thr Glu Ser Ser Phe Cys
1               5

<210> SEQ ID NO 3
<211> LENGTH: 9
<212> TYPE: PRT
<213> ORGANISM: Artificial
<220> FEATURE:
<223> OTHER INFORMATION: synthetic peptide

<400> SEQUENCE: 3

Cys Ser Pro His Thr Lys Asp Trp Cys
1               5

<210> SEQ ID NO 4
<211> LENGTH: 9
<212> TYPE: PRT
<213> ORGANISM: Artificial
<220> FEATURE:
<223> OTHER INFORMATION: synthetic peptide

<400> SEQUENCE: 4

Cys Gly Pro Asp Pro Pro Arg Asp Cys
1               5

<210> SEQ ID NO 5
<211> LENGTH: 9
<212> TYPE: PRT
<213> ORGANISM: Artificial
<220> FEATURE:
<223> OTHER INFORMATION: synthetic peptide

<400> SEQUENCE: 5

Cys Asn Trp His Trp Ile Thr Asn Cys
1               5

<210> SEQ ID NO 6
<211> LENGTH: 9
<212> TYPE: PRT
<213> ORGANISM: Artificial
<220> FEATURE:
<223> OTHER INFORMATION: synthetic peptide

<400> SEQUENCE: 6

Cys Ser Val Ser Gln Val Thr Thr Cys

<210> SEQ ID NO 7
<211> LENGTH: 9
<212> TYPE: PRT
<213> ORGANISM: Artificial
<220> FEATURE:
<223> OTHER INFORMATION: synthetic peptide

<400> SEQUENCE: 7

Cys Glu Gln Thr Leu Thr Pro Gln Cys
1               5

<210> SEQ ID NO 8
<211> LENGTH: 9
<212> TYPE: PRT
<213> ORGANISM: Artificial
<220> FEATURE:
<223> OTHER INFORMATION: synthetic peptide

<400> SEQUENCE: 8

Cys Leu Ser Pro Leu Ser Pro Val Cys
1               5

<210> SEQ ID NO 9
<211> LENGTH: 9
<212> TYPE: PRT
<213> ORGANISM: Artificial
<220> FEATURE:
<223> OTHER INFORMATION: synthetic peptide

<400> SEQUENCE: 9

Cys Leu Thr Ser Ser Val Ser Thr Cys
1               5

<210> SEQ ID NO 10
<211> LENGTH: 9
<212> TYPE: PRT
<213> ORGANISM: Artificial
<220> FEATURE:
<223> OTHER INFORMATION: synthetic peptide

<400> SEQUENCE: 10

Cys Val Asp Ile Pro Ser Phe Gln Cys
1               5

<210> SEQ ID NO 11
<211> LENGTH: 9
<212> TYPE: PRT
<213> ORGANISM: Artificial
<220> FEATURE:
<223> OTHER INFORMATION: synthetic peptide

<400> SEQUENCE: 11

Cys Thr Val Ser Gly His Gln Asp Cys
1               5

<210> SEQ ID NO 12
<211> LENGTH: 9
<212> TYPE: PRT
<213> ORGANISM: Artificial
<220> FEATURE:
<223> OTHER INFORMATION: synthetic peptide

<400> SEQUENCE: 12

Cys Leu His Pro Met Leu Thr Asp Cys
1               5

```
<210> SEQ ID NO 13
<211> LENGTH: 9
<212> TYPE: PRT
<213> ORGANISM: Artificial
<220> FEATURE:
<223> OTHER INFORMATION: synthetic peptide

<400> SEQUENCE: 13

Cys Cys Ala Leu Asp Leu Glu Thr Cys
1               5

<210> SEQ ID NO 14
<211> LENGTH: 9
<212> TYPE: PRT
<213> ORGANISM: Artificial
<220> FEATURE:
<223> OTHER INFORMATION: synthetic peptide

<400> SEQUENCE: 14

Cys Asp Ser Pro Asn His Arg Leu Cys
1               5

<210> SEQ ID NO 15
<211> LENGTH: 9
<212> TYPE: PRT
<213> ORGANISM: Artificial
<220> FEATURE:
<223> OTHER INFORMATION: synthetic peptide

<400> SEQUENCE: 15

Cys Met Thr Ser Phe Asn Leu Ser Cys
1               5

<210> SEQ ID NO 16
<211> LENGTH: 9
<212> TYPE: PRT
<213> ORGANISM: Artificial
<220> FEATURE:
<223> OTHER INFORMATION: synthetic peptide

<400> SEQUENCE: 16

Cys Leu Asn Asn Ser His Ala Glu Cys
1               5

<210> SEQ ID NO 17
<211> LENGTH: 9
<212> TYPE: PRT
<213> ORGANISM: Artificial
<220> FEATURE:
<223> OTHER INFORMATION: synthetic peptide

<400> SEQUENCE: 17

Cys Pro Gln Asn Thr Ala Lys Ala Cys
1               5

<210> SEQ ID NO 18
<211> LENGTH: 9
<212> TYPE: PRT
<213> ORGANISM: Artificial
<220> FEATURE:
<223> OTHER INFORMATION: synthetic peptide

<400> SEQUENCE: 18

Cys Pro Phe Arg Ser His Gln Arg Cys
1               5

<210> SEQ ID NO 19
```

<211> LENGTH: 9
<212> TYPE: PRT
<213> ORGANISM: Artificial
<220> FEATURE:
<223> OTHER INFORMATION: synthetic peptide

<400> SEQUENCE: 19

Cys Pro Leu Leu Pro Trp Ser Pro Cys
1               5

<210> SEQ ID NO 20
<211> LENGTH: 9
<212> TYPE: PRT
<213> ORGANISM: Artificial
<220> FEATURE:
<223> OTHER INFORMATION: synthetic peptide

<400> SEQUENCE: 20

Cys Ser Ser Ile Pro Gly Pro Ser Cys
1               5

<210> SEQ ID NO 21
<211> LENGTH: 9
<212> TYPE: PRT
<213> ORGANISM: Artificial
<220> FEATURE:
<223> OTHER INFORMATION: synthetic peptide

<400> SEQUENCE: 21

Cys Val Asn Thr Ser Ser Asp Ser Cys
1               5

<210> SEQ ID NO 22
<211> LENGTH: 9
<212> TYPE: PRT
<213> ORGANISM: Artificial
<220> FEATURE:
<223> OTHER INFORMATION: synthetic peptide

<400> SEQUENCE: 22

Cys Pro Ser Arg Thr Pro Asn His Cys
1               5

<210> SEQ ID NO 23
<211> LENGTH: 9
<212> TYPE: PRT
<213> ORGANISM: Artificial
<220> FEATURE:
<223> OTHER INFORMATION: synthetic peptide

<400> SEQUENCE: 23

Cys Tyr Ser His Asn Leu Ala Glu Cys
1               5

<210> SEQ ID NO 24
<211> LENGTH: 9
<212> TYPE: PRT
<213> ORGANISM: Artificial
<220> FEATURE:
<223> OTHER INFORMATION: synthetic peptide

<400> SEQUENCE: 24

Cys Thr Pro Pro Lys Thr Arg Thr Cys
1               5

<210> SEQ ID NO 25
<211> LENGTH: 9
<212> TYPE: PRT

```
<213> ORGANISM: Artificial
<220> FEATURE:
<223> OTHER INFORMATION: synthetic peptide

<400> SEQUENCE: 25

Cys Asp Pro Met Arg Pro Ser Met Cys
1               5

<210> SEQ ID NO 26
<211> LENGTH: 9
<212> TYPE: PRT
<213> ORGANISM: Artificial
<220> FEATURE:
<223> OTHER INFORMATION: synthetic peptide

<400> SEQUENCE: 26

Cys Pro Arg Leu Ser Gln Ser Pro Cys
1               5

<210> SEQ ID NO 27
<211> LENGTH: 9
<212> TYPE: PRT
<213> ORGANISM: Artificial
<220> FEATURE:
<223> OTHER INFORMATION: synthetic peptide

<400> SEQUENCE: 27

Cys Ser Leu Asp Tyr Pro Asp Ser Cys
1               5

<210> SEQ ID NO 28
<211> LENGTH: 7
<212> TYPE: PRT
<213> ORGANISM: Artificial
<220> FEATURE:
<223> OTHER INFORMATION: synthetic peptide

<400> SEQUENCE: 28

Ser His Val Gln Cys Val Asn
1               5

<210> SEQ ID NO 29
<211> LENGTH: 7
<212> TYPE: PRT
<213> ORGANISM: Artificial
<220> FEATURE:
<223> OTHER INFORMATION: synthetic peptide

<400> SEQUENCE: 29

Ile Pro Asn Pro Ser Ile Arg
1               5

<210> SEQ ID NO 30
<211> LENGTH: 7
<212> TYPE: PRT
<213> ORGANISM: Artificial
<220> FEATURE:
<223> OTHER INFORMATION: synthetic peptide

<400> SEQUENCE: 30

Arg Ile Arg Val Ile Arg Glu
1               5

<210> SEQ ID NO 31
<211> LENGTH: 7
<212> TYPE: PRT
<213> ORGANISM: Artificial
<220> FEATURE:
```

<223> OTHER INFORMATION: synthetic peptide

<400> SEQUENCE: 31

Glu Tyr Asp Asn Ser Pro Pro
1               5

<210> SEQ ID NO 32
<211> LENGTH: 7
<212> TYPE: PRT
<213> ORGANISM: Artificial
<220> FEATURE:
<223> OTHER INFORMATION: synthetic peptide

<400> SEQUENCE: 32

Arg Thr Glu His Ala Gly Phe
1               5

<210> SEQ ID NO 33
<211> LENGTH: 7
<212> TYPE: PRT
<213> ORGANISM: Artificial
<220> FEATURE:
<223> OTHER INFORMATION: synthetic peptide

<400> SEQUENCE: 33

Tyr Val Ser Asp Tyr Asp Trp
1               5

<210> SEQ ID NO 34
<211> LENGTH: 7
<212> TYPE: PRT
<213> ORGANISM: Artificial
<220> FEATURE:
<223> OTHER INFORMATION: synthetic peptide

<400> SEQUENCE: 34

Ser Asp Arg Pro Ser Leu Lys
1               5

<210> SEQ ID NO 35
<211> LENGTH: 7
<212> TYPE: PRT
<213> ORGANISM: Artificial
<220> FEATURE:
<223> OTHER INFORMATION: synthetic peptide

<400> SEQUENCE: 35

Tyr Trp Ser Pro Ser Leu Lys
1               5

<210> SEQ ID NO 36
<211> LENGTH: 7
<212> TYPE: PRT
<213> ORGANISM: Artificial
<220> FEATURE:
<223> OTHER INFORMATION: synthetic peptide

<400> SEQUENCE: 36

Leu Pro Leu Lys Leu Leu Trp
1               5

<210> SEQ ID NO 37
<211> LENGTH: 7
<212> TYPE: PRT
<213> ORGANISM: Artificial
<220> FEATURE:
<223> OTHER INFORMATION: synthetic peptide

```
<400> SEQUENCE: 37

His Ala His Lys Val Gly Thr
1               5

<210> SEQ ID NO 38
<211> LENGTH: 7
<212> TYPE: PRT
<213> ORGANISM: Artificial
<220> FEATURE:
<223> OTHER INFORMATION: synthetic peptide

<400> SEQUENCE: 38

Ala Leu Lys Pro Met Ser His
1               5

<210> SEQ ID NO 39
<211> LENGTH: 7
<212> TYPE: PRT
<213> ORGANISM: Artificial
<220> FEATURE:
<223> OTHER INFORMATION: synthetic peptide

<400> SEQUENCE: 39

Thr Pro Asp Tyr Leu Ala Ala
1               5

<210> SEQ ID NO 40
<211> LENGTH: 7
<212> TYPE: PRT
<213> ORGANISM: Artificial
<220> FEATURE:
<223> OTHER INFORMATION: synthetic peptide

<400> SEQUENCE: 40

Thr Pro Pro Ala Ala Ala Arg
1               5

<210> SEQ ID NO 41
<211> LENGTH: 7
<212> TYPE: PRT
<213> ORGANISM: Artificial
<220> FEATURE:
<223> OTHER INFORMATION: synthetic peptide

<400> SEQUENCE: 41

Tyr Pro Ser Thr Phe Thr Arg
1               5

<210> SEQ ID NO 42
<211> LENGTH: 7
<212> TYPE: PRT
<213> ORGANISM: Artificial
<220> FEATURE:
<223> OTHER INFORMATION: synthetic peptide

<400> SEQUENCE: 42

Val Cys Arg Pro Pro Cys Pro
1               5

<210> SEQ ID NO 43
<211> LENGTH: 7
<212> TYPE: PRT
<213> ORGANISM: Artificial
<220> FEATURE:
<223> OTHER INFORMATION: synthetic peptide

<400> SEQUENCE: 43
```

```
Met Pro Leu Pro Phe Pro Thr
1               5
```

<210> SEQ ID NO 44
<211> LENGTH: 7
<212> TYPE: PRT
<213> ORGANISM: Artificial
<220> FEATURE:
<223> OTHER INFORMATION: synthetic peptide

<400> SEQUENCE: 44

```
Ala Ser Asp Thr Ile Gln Thr
1               5
```

<210> SEQ ID NO 45
<211> LENGTH: 7
<212> TYPE: PRT
<213> ORGANISM: Artificial
<220> FEATURE:
<223> OTHER INFORMATION: synthetic peptide

<400> SEQUENCE: 45

```
Ser Tyr Tyr Met Arg Asp Pro
1               5
```

<210> SEQ ID NO 46
<211> LENGTH: 7
<212> TYPE: PRT
<213> ORGANISM: Artificial
<220> FEATURE:
<223> OTHER INFORMATION: synthetic peptide

<400> SEQUENCE: 46

```
Ser Gln Asp Pro Ser Gln Leu
1               5
```

<210> SEQ ID NO 47
<211> LENGTH: 7
<212> TYPE: PRT
<213> ORGANISM: Artificial
<220> FEATURE:
<223> OTHER INFORMATION: synthetic peptide

<400> SEQUENCE: 47

```
Leu Gln Thr Phe Pro Lys Pro
1               5
```

<210> SEQ ID NO 48
<211> LENGTH: 7
<212> TYPE: PRT
<213> ORGANISM: Artificial
<220> FEATURE:
<223> OTHER INFORMATION: synthetic peptide

<400> SEQUENCE: 48

```
Leu Ser Asn Thr Phe Gly Leu
1               5
```

<210> SEQ ID NO 49
<211> LENGTH: 7
<212> TYPE: PRT
<213> ORGANISM: Artificial
<220> FEATURE:
<223> OTHER INFORMATION: synthetic peptide

<400> SEQUENCE: 49

```
Ile Pro Trp Ala Ser Leu Leu
1               5
```

```
<210> SEQ ID NO 50
<211> LENGTH: 7
<212> TYPE: PRT
<213> ORGANISM: Artificial
<220> FEATURE:
<223> OTHER INFORMATION: synthetic peptide

<400> SEQUENCE: 50

Ile Thr Ala Asn Thr Leu Ser
1               5

<210> SEQ ID NO 51
<211> LENGTH: 7
<212> TYPE: PRT
<213> ORGANISM: Artificial
<220> FEATURE:
<223> OTHER INFORMATION: synthetic peptide

<400> SEQUENCE: 51

Lys Ile Ser Leu Gly Gly Leu
1               5

<210> SEQ ID NO 52
<211> LENGTH: 7
<212> TYPE: PRT
<213> ORGANISM: Artificial
<220> FEATURE:
<223> OTHER INFORMATION: synthetic peptide

<400> SEQUENCE: 52

Ala Pro Gln Pro Tyr Arg Gln
1               5

<210> SEQ ID NO 53
<211> LENGTH: 7
<212> TYPE: PRT
<213> ORGANISM: Artificial
<220> FEATURE:
<223> OTHER INFORMATION: synthetic peptide

<400> SEQUENCE: 53

His Ser Pro Ala Asp Thr Pro
1               5

<210> SEQ ID NO 54
<211> LENGTH: 7
<212> TYPE: PRT
<213> ORGANISM: Artificial
<220> FEATURE:
<223> OTHER INFORMATION: synthetic peptide

<400> SEQUENCE: 54

Thr Leu Pro Ala Leu Ala Leu
1               5

<210> SEQ ID NO 55
<211> LENGTH: 7
<212> TYPE: PRT
<213> ORGANISM: Artificial
<220> FEATURE:
<223> OTHER INFORMATION: synthetic peptide

<400> SEQUENCE: 55

Asn Ala Gln Lys Ser Thr Leu
1               5
```

```
<210> SEQ ID NO 56
<211> LENGTH: 7
<212> TYPE: PRT
<213> ORGANISM: Artificial
<220> FEATURE:
<223> OTHER INFORMATION: synthetic peptide

<400> SEQUENCE: 56

Ala Asp Glu Ala Leu Thr Leu
1               5

<210> SEQ ID NO 57
<211> LENGTH: 7
<212> TYPE: PRT
<213> ORGANISM: Artificial
<220> FEATURE:
<223> OTHER INFORMATION: synthetic peptide

<400> SEQUENCE: 57

Ser Leu Ser Ala Ser Arg Ile
1               5

<210> SEQ ID NO 58
<211> LENGTH: 7
<212> TYPE: PRT
<213> ORGANISM: Artificial
<220> FEATURE:
<223> OTHER INFORMATION: synthetic peptide

<400> SEQUENCE: 58

Gly Ser Ala Ser Ala Leu Ala
1               5

<210> SEQ ID NO 59
<211> LENGTH: 7
<212> TYPE: PRT
<213> ORGANISM: Artificial
<220> FEATURE:
<223> OTHER INFORMATION: synthetic peptide

<400> SEQUENCE: 59

Ser Asn Leu Ser Gly Ser Thr
1               5

<210> SEQ ID NO 60
<211> LENGTH: 7
<212> TYPE: PRT
<213> ORGANISM: Artificial
<220> FEATURE:
<223> OTHER INFORMATION: synthetic peptide

<400> SEQUENCE: 60

Gln Val Pro Val His Pro Ser
1               5

<210> SEQ ID NO 61
<211> LENGTH: 7
<212> TYPE: PRT
<213> ORGANISM: Artificial
<220> FEATURE:
<223> OTHER INFORMATION: synthetic peptide

<400> SEQUENCE: 61

Ile Pro Gly Thr Val His Val
1               5

<210> SEQ ID NO 62
<211> LENGTH: 7
```

```
<212> TYPE: PRT
<213> ORGANISM: Artificial
<220> FEATURE:
<223> OTHER INFORMATION: synthetic peptide

<400> SEQUENCE: 62

Thr Thr Thr Ser Phe Arg Ala
1               5

<210> SEQ ID NO 63
<211> LENGTH: 7
<212> TYPE: PRT
<213> ORGANISM: Artificial
<220> FEATURE:
<223> OTHER INFORMATION: synthetic peptide

<400> SEQUENCE: 63

Ala Thr Ser Leu Val Asn Leu
1               5

<210> SEQ ID NO 64
<211> LENGTH: 7
<212> TYPE: PRT
<213> ORGANISM: Artificial
<220> FEATURE:
<223> OTHER INFORMATION: synthetic peptide

<400> SEQUENCE: 64

Ala Ser Gly Met Val Phe Met
1               5

<210> SEQ ID NO 65
<211> LENGTH: 7
<212> TYPE: PRT
<213> ORGANISM: Artificial
<220> FEATURE:
<223> OTHER INFORMATION: synthetic peptide

<400> SEQUENCE: 65

Gln Leu Phe Pro Cys Met Ser
1               5

<210> SEQ ID NO 66
<211> LENGTH: 7
<212> TYPE: PRT
<213> ORGANISM: Artificial
<220> FEATURE:
<223> OTHER INFORMATION: synthetic peptide

<400> SEQUENCE: 66

Leu Ile Thr His Pro Ile Val
1               5

<210> SEQ ID NO 67
<211> LENGTH: 7
<212> TYPE: PRT
<213> ORGANISM: Artificial
<220> FEATURE:
<223> OTHER INFORMATION: synthetic peptide

<400> SEQUENCE: 67

Tyr Thr Leu Gly Asp Pro Ser
1               5

<210> SEQ ID NO 68
<211> LENGTH: 7
<212> TYPE: PRT
<213> ORGANISM: Artificial
```

```
<220> FEATURE:
<223> OTHER INFORMATION: synthetic peptide

<400> SEQUENCE: 68

Leu Arg Pro Met Thr Val Pro
1               5

<210> SEQ ID NO 69
<211> LENGTH: 7
<212> TYPE: PRT
<213> ORGANISM: Artificial
<220> FEATURE:
<223> OTHER INFORMATION: synthetic peptide

<400> SEQUENCE: 69

Leu Gly Thr Thr Pro Gln Leu
1               5

<210> SEQ ID NO 70
<211> LENGTH: 7
<212> TYPE: PRT
<213> ORGANISM: Artificial
<220> FEATURE:
<223> OTHER INFORMATION: synthetic peptide

<400> SEQUENCE: 70

Thr Ala Phe Leu Gly Gln His
1               5

<210> SEQ ID NO 71
<211> LENGTH: 7
<212> TYPE: PRT
<213> ORGANISM: Artificial
<220> FEATURE:
<223> OTHER INFORMATION: synthetic peptide

<400> SEQUENCE: 71

Tyr His Gln Arg Gly Pro Val
1               5

<210> SEQ ID NO 72
<211> LENGTH: 7
<212> TYPE: PRT
<213> ORGANISM: Artificial
<220> FEATURE:
<223> OTHER INFORMATION: synthetic peptide

<400> SEQUENCE: 72

Ser His Leu Lys Ser Met Ser
1               5

<210> SEQ ID NO 73
<211> LENGTH: 7
<212> TYPE: PRT
<213> ORGANISM: Artificial
<220> FEATURE:
<223> OTHER INFORMATION: synthetic peptide

<400> SEQUENCE: 73

His Met Ser Arg Met Ala Asn
1               5

<210> SEQ ID NO 74
<211> LENGTH: 7
<212> TYPE: PRT
<213> ORGANISM: Artificial
<220> FEATURE:
<223> OTHER INFORMATION: synthetic peptide
```

```
<400> SEQUENCE: 74

Ala Ser Thr Gln Leu Leu Pro
1               5

<210> SEQ ID NO 75
<211> LENGTH: 7
<212> TYPE: PRT
<213> ORGANISM: Artificial
<220> FEATURE:
<223> OTHER INFORMATION: synthetic peptide

<400> SEQUENCE: 75

Ser Ala Leu Trp Ser Pro Val
1               5

<210> SEQ ID NO 76
<211> LENGTH: 7
<212> TYPE: PRT
<213> ORGANISM: Artificial
<220> FEATURE:
<223> OTHER INFORMATION: synthetic peptide

<400> SEQUENCE: 76

Val Leu Glu Tyr Ser Pro Ser
1               5

<210> SEQ ID NO 77
<211> LENGTH: 7
<212> TYPE: PRT
<213> ORGANISM: Artificial
<220> FEATURE:
<223> OTHER INFORMATION: synthetic peptide

<400> SEQUENCE: 77

Ser Gln Pro Ala Thr Lys Arg
1               5

<210> SEQ ID NO 78
<211> LENGTH: 7
<212> TYPE: PRT
<213> ORGANISM: Artificial
<220> FEATURE:
<223> OTHER INFORMATION: synthetic peptide

<400> SEQUENCE: 78

Asp Pro Lys Val Arg Thr Ala
1               5

<210> SEQ ID NO 79
<211> LENGTH: 7
<212> TYPE: PRT
<213> ORGANISM: Artificial
<220> FEATURE:
<223> OTHER INFORMATION: synthetic peptide

<400> SEQUENCE: 79

Phe Glu Arg Asp Leu Pro Trp
1               5

<210> SEQ ID NO 80
<211> LENGTH: 7
<212> TYPE: PRT
<213> ORGANISM: Artificial
<220> FEATURE:
<223> OTHER INFORMATION: synthetic peptide

<400> SEQUENCE: 80
```

```
Asn Arg Ala Gln Asn Arg Lys
1               5

<210> SEQ ID NO 81
<211> LENGTH: 7
<212> TYPE: PRT
<213> ORGANISM: Artificial
<220> FEATURE:
<223> OTHER INFORMATION: synthetic peptide

<400> SEQUENCE: 81

Ala Tyr Pro Phe Ile Phe Arg
1               5

<210> SEQ ID NO 82
<211> LENGTH: 7
<212> TYPE: PRT
<213> ORGANISM: Artificial
<220> FEATURE:
<223> OTHER INFORMATION: synthetic peptide

<400> SEQUENCE: 82

Leu Gly Ile Leu Cys Ser Arg
1               5

<210> SEQ ID NO 83
<211> LENGTH: 7
<212> TYPE: PRT
<213> ORGANISM: Artificial
<220> FEATURE:
<223> OTHER INFORMATION: synthetic peptide

<400> SEQUENCE: 83

Gly Glu Tyr Val Thr Leu Arg
1               5

<210> SEQ ID NO 84
<211> LENGTH: 7
<212> TYPE: PRT
<213> ORGANISM: Artificial
<220> FEATURE:
<223> OTHER INFORMATION: synthetic peptide

<400> SEQUENCE: 84

His Leu Asp Ser Ser Asn Ser
1               5

<210> SEQ ID NO 85
<211> LENGTH: 7
<212> TYPE: PRT
<213> ORGANISM: Artificial
<220> FEATURE:
<223> OTHER INFORMATION: synthetic peptide

<400> SEQUENCE: 85

Leu Asn Thr Ala Arg His Thr
1               5

<210> SEQ ID NO 86
<211> LENGTH: 7
<212> TYPE: PRT
<213> ORGANISM: Artificial
<220> FEATURE:
<223> OTHER INFORMATION: synthetic peptide

<400> SEQUENCE: 86

Thr Ser Val Leu Arg Pro Gly
```

<210> SEQ ID NO 87
<211> LENGTH: 7
<212> TYPE: PRT
<213> ORGANISM: Artificial
<220> FEATURE:
<223> OTHER INFORMATION: synthetic peptide

<400> SEQUENCE: 87

His Val Pro Pro His Ala Arg
1               5

<210> SEQ ID NO 88
<211> LENGTH: 7
<212> TYPE: PRT
<213> ORGANISM: Artificial
<220> FEATURE:
<223> OTHER INFORMATION: synthetic peptide

<400> SEQUENCE: 88

Gly Pro Arg Thr His Asn Ser
1               5

<210> SEQ ID NO 89
<211> LENGTH: 7
<212> TYPE: PRT
<213> ORGANISM: Artificial
<220> FEATURE:
<223> OTHER INFORMATION: synthetic peptide

<400> SEQUENCE: 89

Gln Met Pro Ala Val Pro Ser
1               5

<210> SEQ ID NO 90
<211> LENGTH: 7
<212> TYPE: PRT
<213> ORGANISM: Artificial
<220> FEATURE:
<223> OTHER INFORMATION: synthetic peptide

<400> SEQUENCE: 90

Trp Asn Pro Thr Tyr Pro Pro
1               5

<210> SEQ ID NO 91
<211> LENGTH: 7
<212> TYPE: PRT
<213> ORGANISM: Artificial
<220> FEATURE:
<223> OTHER INFORMATION: synthetic peptide

<400> SEQUENCE: 91

His Gln Asp Leu Arg Arg Gln
1               5

<210> SEQ ID NO 92
<211> LENGTH: 7
<212> TYPE: PRT
<213> ORGANISM: Artificial
<220> FEATURE:
<223> OTHER INFORMATION: synthetic peptide

<400> SEQUENCE: 92

Gly Glu Leu Pro Phe Asn Pro
1               5

<210> SEQ ID NO 93
<211> LENGTH: 7
<212> TYPE: PRT
<213> ORGANISM: Artificial
<220> FEATURE:
<223> OTHER INFORMATION: synthetic peptide

<400> SEQUENCE: 93

Ser Tyr Leu Gln Leu Pro Pro
1               5

<210> SEQ ID NO 94
<211> LENGTH: 7
<212> TYPE: PRT
<213> ORGANISM: Artificial
<220> FEATURE:
<223> OTHER INFORMATION: synthetic peptide

<400> SEQUENCE: 94

His Val Leu Pro Val Pro Leu
1               5

<210> SEQ ID NO 95
<211> LENGTH: 7
<212> TYPE: PRT
<213> ORGANISM: Artificial
<220> FEATURE:
<223> OTHER INFORMATION: synthetic peptide

<400> SEQUENCE: 95

Ala Ser Thr Tyr Leu Leu Gly
1               5

<210> SEQ ID NO 96
<211> LENGTH: 7
<212> TYPE: PRT
<213> ORGANISM: Artificial
<220> FEATURE:
<223> OTHER INFORMATION: synthetic peptide

<400> SEQUENCE: 96

Tyr Glu Arg Ala Gly Ser His
1               5

<210> SEQ ID NO 97
<211> LENGTH: 7
<212> TYPE: PRT
<213> ORGANISM: Artificial
<220> FEATURE:
<223> OTHER INFORMATION: synthetic peptide

<400> SEQUENCE: 97

Trp Gln Pro His Ser His Pro
1               5

<210> SEQ ID NO 98
<211> LENGTH: 7
<212> TYPE: PRT
<213> ORGANISM: Artificial
<220> FEATURE:
<223> OTHER INFORMATION: synthetic peptide

<400> SEQUENCE: 98

Asp Ser Leu Thr Pro Glu Thr
1               5

<210> SEQ ID NO 99

<211> LENGTH: 7
<212> TYPE: PRT
<213> ORGANISM: Artificial
<220> FEATURE:
<223> OTHER INFORMATION: synthetic peptide

<400> SEQUENCE: 99

His Pro Asn Arg Phe Asp His
1               5

<210> SEQ ID NO 100
<211> LENGTH: 7
<212> TYPE: PRT
<213> ORGANISM: Artificial
<220> FEATURE:
<223> OTHER INFORMATION: synthetic peptide

<400> SEQUENCE: 100

Asn Asn Ala Ile Leu His Pro
1               5

<210> SEQ ID NO 101
<211> LENGTH: 7
<212> TYPE: PRT
<213> ORGANISM: Artificial
<220> FEATURE:
<223> OTHER INFORMATION: synthetic peptide

<400> SEQUENCE: 101

Arg Leu Pro Gly His Pro Ser
1               5

<210> SEQ ID NO 102
<211> LENGTH: 7
<212> TYPE: PRT
<213> ORGANISM: Artificial
<220> FEATURE:
<223> OTHER INFORMATION: synthetic peptide

<400> SEQUENCE: 102

His Ala Pro His Leu Trp Asp
1               5

<210> SEQ ID NO 103
<211> LENGTH: 7
<212> TYPE: PRT
<213> ORGANISM: Artificial
<220> FEATURE:
<223> OTHER INFORMATION: synthetic peptide

<400> SEQUENCE: 103

Ser Pro Asn Val Pro Pro Tyr
1               5

<210> SEQ ID NO 104
<211> LENGTH: 7
<212> TYPE: PRT
<213> ORGANISM: Artificial
<220> FEATURE:
<223> OTHER INFORMATION: synthetic peptide

<400> SEQUENCE: 104

Ile Pro His Leu Ser Thr Leu
1               5

<210> SEQ ID NO 105
<211> LENGTH: 7
<212> TYPE: PRT

```
<213> ORGANISM: Artificial
<220> FEATURE:
<223> OTHER INFORMATION: synthetic peptide

<400> SEQUENCE: 105

Asp Tyr Pro Ala Ser Ser Phe
1               5

<210> SEQ ID NO 106
<211> LENGTH: 7
<212> TYPE: PRT
<213> ORGANISM: Artificial
<220> FEATURE:
<223> OTHER INFORMATION: synthetic peptide

<400> SEQUENCE: 106

Phe Pro Arg Met Gln Pro Leu
1               5

<210> SEQ ID NO 107
<211> LENGTH: 7
<212> TYPE: PRT
<213> ORGANISM: Artificial
<220> FEATURE:
<223> OTHER INFORMATION: synthetic peptide

<400> SEQUENCE: 107

His Asn Lys Thr Ser Tyr Tyr
1               5

<210> SEQ ID NO 108
<211> LENGTH: 7
<212> TYPE: PRT
<213> ORGANISM: Artificial
<220> FEATURE:
<223> OTHER INFORMATION: synthetic peptide

<400> SEQUENCE: 108

Thr His His Pro Ile His Lys
1               5

<210> SEQ ID NO 109
<211> LENGTH: 7
<212> TYPE: PRT
<213> ORGANISM: Artificial
<220> FEATURE:
<223> OTHER INFORMATION: synthetic peptide

<400> SEQUENCE: 109

Thr Ser Pro Leu Pro Tyr Trp
1               5

<210> SEQ ID NO 110
<211> LENGTH: 7
<212> TYPE: PRT
<213> ORGANISM: Artificial
<220> FEATURE:
<223> OTHER INFORMATION: synthetic peptide

<400> SEQUENCE: 110

Ala Ser Pro His Pro Ala Val
1               5

<210> SEQ ID NO 111
<211> LENGTH: 7
<212> TYPE: PRT
<213> ORGANISM: Artificial
<220> FEATURE:
```

```
<223> OTHER INFORMATION: synthetic peptide

<400> SEQUENCE: 111

Tyr Ser Leu Gln His Met Leu
1               5

<210> SEQ ID NO 112
<211> LENGTH: 7
<212> TYPE: PRT
<213> ORGANISM: Artificial
<220> FEATURE:
<223> OTHER INFORMATION: synthetic peptide

<400> SEQUENCE: 112

Phe Pro Thr Thr Tyr Trp Ile
1               5

<210> SEQ ID NO 113
<211> LENGTH: 7
<212> TYPE: PRT
<213> ORGANISM: Artificial
<220> FEATURE:
<223> OTHER INFORMATION: synthetic peptide

<400> SEQUENCE: 113

Cys Leu Arg Ala Met Asn Asp
1               5

<210> SEQ ID NO 114
<211> LENGTH: 7
<212> TYPE: PRT
<213> ORGANISM: Artificial
<220> FEATURE:
<223> OTHER INFORMATION: synthetic peptide

<400> SEQUENCE: 114

Asn Lys Leu Pro Pro Leu Phe
1               5

<210> SEQ ID NO 115
<211> LENGTH: 7
<212> TYPE: PRT
<213> ORGANISM: Artificial
<220> FEATURE:
<223> OTHER INFORMATION: synthetic peptide

<400> SEQUENCE: 115

Ser Gly Leu Gln Gln Pro Arg
1               5

<210> SEQ ID NO 116
<211> LENGTH: 7
<212> TYPE: PRT
<213> ORGANISM: Artificial
<220> FEATURE:
<223> OTHER INFORMATION: synthetic peptide

<400> SEQUENCE: 116

Gln Ala Thr Lys Val Arg Ser
1               5

<210> SEQ ID NO 117
<211> LENGTH: 7
<212> TYPE: PRT
<213> ORGANISM: Artificial
<220> FEATURE:
<223> OTHER INFORMATION: synthetic peptide
```

```
<400> SEQUENCE: 117

Ser Pro Thr Ser Ala Arg Ser
1               5

<210> SEQ ID NO 118
<211> LENGTH: 7
<212> TYPE: PRT
<213> ORGANISM: Artificial
<220> FEATURE:
<223> OTHER INFORMATION: synthetic peptide

<400> SEQUENCE: 118

Ala Ser His Pro Ser Ser Ala
1               5

<210> SEQ ID NO 119
<211> LENGTH: 7
<212> TYPE: PRT
<213> ORGANISM: Artificial
<220> FEATURE:
<223> OTHER INFORMATION: synthetic peptide

<400> SEQUENCE: 119

Gln Pro Ile Gly Ala Gln Arg
1               5

<210> SEQ ID NO 120
<211> LENGTH: 7
<212> TYPE: PRT
<213> ORGANISM: Artificial
<220> FEATURE:
<223> OTHER INFORMATION: synthetic peptide

<400> SEQUENCE: 120

Leu Asp Thr His His Leu Gln
1               5

<210> SEQ ID NO 121
<211> LENGTH: 7
<212> TYPE: PRT
<213> ORGANISM: Artificial
<220> FEATURE:
<223> OTHER INFORMATION: synthetic peptide

<400> SEQUENCE: 121

Gln Pro Ser Leu His Ile Ser
1               5

<210> SEQ ID NO 122
<211> LENGTH: 7
<212> TYPE: PRT
<213> ORGANISM: Artificial
<220> FEATURE:
<223> OTHER INFORMATION: synthetic peptide

<400> SEQUENCE: 122

Ser Ser Phe Leu Leu Gly Trp
1               5

<210> SEQ ID NO 123
<211> LENGTH: 7
<212> TYPE: PRT
<213> ORGANISM: Artificial
<220> FEATURE:
<223> OTHER INFORMATION: synthetic peptide

<400> SEQUENCE: 123
```

```
Ser Gln Gln Leu Ala Ser Ala
1               5

<210> SEQ ID NO 124
<211> LENGTH: 7
<212> TYPE: PRT
<213> ORGANISM: Artificial
<220> FEATURE:
<223> OTHER INFORMATION: synthetic peptide

<400> SEQUENCE: 124

Gln Pro Leu Arg Ala Gly Ser
1               5

<210> SEQ ID NO 125
<211> LENGTH: 7
<212> TYPE: PRT
<213> ORGANISM: Artificial
<220> FEATURE:
<223> OTHER INFORMATION: synthetic peptide

<400> SEQUENCE: 125

Glu Pro Leu Arg Arg Asp Thr
1               5

<210> SEQ ID NO 126
<211> LENGTH: 7
<212> TYPE: PRT
<213> ORGANISM: Artificial
<220> FEATURE:
<223> OTHER INFORMATION: synthetic peptide

<400> SEQUENCE: 126

Ala Pro Phe Leu Ser Arg Leu
1               5

<210> SEQ ID NO 127
<211> LENGTH: 7
<212> TYPE: PRT
<213> ORGANISM: Artificial
<220> FEATURE:
<223> OTHER INFORMATION: synthetic peptide

<400> SEQUENCE: 127

Ile Pro His Leu Lys Leu Pro
1               5

<210> SEQ ID NO 128
<211> LENGTH: 7
<212> TYPE: PRT
<213> ORGANISM: Artificial
<220> FEATURE:
<223> OTHER INFORMATION: synthetic peptide

<400> SEQUENCE: 128

Leu Pro Met Tyr Ser Val Gln
1               5

<210> SEQ ID NO 129
<211> LENGTH: 7
<212> TYPE: PRT
<213> ORGANISM: Artificial
<220> FEATURE:
<223> OTHER INFORMATION: synthetic peptide

<400> SEQUENCE: 129

Met Leu Pro Ser Cys Ala Asp
1               5
```

```
<210> SEQ ID NO 130
<211> LENGTH: 7
<212> TYPE: PRT
<213> ORGANISM: Artificial
<220> FEATURE:
<223> OTHER INFORMATION: synthetic peptide

<400> SEQUENCE: 130

Leu Leu Leu Thr Ser Pro Gly
1               5

<210> SEQ ID NO 131
<211> LENGTH: 7
<212> TYPE: PRT
<213> ORGANISM: Artificial
<220> FEATURE:
<223> OTHER INFORMATION: synthetic peptide

<400> SEQUENCE: 131

Ser Pro Ala Gly Ala Tyr Tyr
1               5

<210> SEQ ID NO 132
<211> LENGTH: 7
<212> TYPE: PRT
<213> ORGANISM: Artificial
<220> FEATURE:
<223> OTHER INFORMATION: synthetic peptide

<400> SEQUENCE: 132

Thr Gly Pro Met Pro Ala Pro
1               5

<210> SEQ ID NO 133
<211> LENGTH: 7
<212> TYPE: PRT
<213> ORGANISM: Artificial
<220> FEATURE:
<223> OTHER INFORMATION: synthetic peptide

<400> SEQUENCE: 133

Tyr Lys Ser Thr Leu Asn Asn
1               5

<210> SEQ ID NO 134
<211> LENGTH: 7
<212> TYPE: PRT
<213> ORGANISM: Artificial
<220> FEATURE:
<223> OTHER INFORMATION: synthetic peptide

<400> SEQUENCE: 134

Ser Leu Ser Val Ser Thr Arg
1               5

<210> SEQ ID NO 135
<211> LENGTH: 7
<212> TYPE: PRT
<213> ORGANISM: Artificial
<220> FEATURE:
<223> OTHER INFORMATION: synthetic peptide

<400> SEQUENCE: 135

Arg Pro Leu Gln Asn Asn Tyr
1               5
```

```
<210> SEQ ID NO 136
<211> LENGTH: 7
<212> TYPE: PRT
<213> ORGANISM: Artificial
<220> FEATURE:
<223> OTHER INFORMATION: synthetic peptide

<400> SEQUENCE: 136

Val Val Thr Leu Ser Thr Leu
1               5

<210> SEQ ID NO 137
<211> LENGTH: 7
<212> TYPE: PRT
<213> ORGANISM: Artificial
<220> FEATURE:
<223> OTHER INFORMATION: synthetic peptide

<400> SEQUENCE: 137

His Asn Leu His Gly Asn Leu
1               5

<210> SEQ ID NO 138
<211> LENGTH: 7
<212> TYPE: PRT
<213> ORGANISM: Artificial
<220> FEATURE:
<223> OTHER INFORMATION: synthetic peptide

<400> SEQUENCE: 138

Thr His Gln Cys Arg Gln Cys
1               5

<210> SEQ ID NO 139
<211> LENGTH: 7
<212> TYPE: PRT
<213> ORGANISM: Artificial
<220> FEATURE:
<223> OTHER INFORMATION: synthetic peptide

<400> SEQUENCE: 139

Val Ser Pro Phe Ile Arg Ser
1               5

<210> SEQ ID NO 140
<211> LENGTH: 7
<212> TYPE: PRT
<213> ORGANISM: Artificial
<220> FEATURE:
<223> OTHER INFORMATION: synthetic peptide

<400> SEQUENCE: 140

Ala Pro Arg Thr Ala Phe Pro
1               5

<210> SEQ ID NO 141
<211> LENGTH: 7
<212> TYPE: PRT
<213> ORGANISM: Artificial
<220> FEATURE:
<223> OTHER INFORMATION: synthetic peptide

<400> SEQUENCE: 141

His Gly Thr Met Thr Val Met
1               5

<210> SEQ ID NO 142
<211> LENGTH: 7
```

```
<212> TYPE: PRT
<213> ORGANISM: Artificial
<220> FEATURE:
<223> OTHER INFORMATION: synthetic peptide

<400> SEQUENCE: 142

Asn Arg Leu Ala Gln Val His
1               5

<210> SEQ ID NO 143
<211> LENGTH: 7
<212> TYPE: PRT
<213> ORGANISM: Artificial
<220> FEATURE:
<223> OTHER INFORMATION: synthetic peptide

<400> SEQUENCE: 143

Ala Leu Leu Ala Leu Ile Pro
1               5

<210> SEQ ID NO 144
<211> LENGTH: 7
<212> TYPE: PRT
<213> ORGANISM: Artificial
<220> FEATURE:
<223> OTHER INFORMATION: synthetic peptide

<400> SEQUENCE: 144

Leu Pro Tyr Gly Arg Gln His
1               5

<210> SEQ ID NO 145
<211> LENGTH: 7
<212> TYPE: PRT
<213> ORGANISM: Artificial
<220> FEATURE:
<223> OTHER INFORMATION: synthetic peptide

<400> SEQUENCE: 145

Ala Arg Ala Thr His Pro Pro
1               5

<210> SEQ ID NO 146
<211> LENGTH: 7
<212> TYPE: PRT
<213> ORGANISM: Artificial
<220> FEATURE:
<223> OTHER INFORMATION: synthetic peptide

<400> SEQUENCE: 146

Leu Gln Pro Trp Val Thr Pro
1               5

<210> SEQ ID NO 147
<211> LENGTH: 7
<212> TYPE: PRT
<213> ORGANISM: Artificial
<220> FEATURE:
<223> OTHER INFORMATION: synthetic peptide

<400> SEQUENCE: 147

Arg Gly Ile Thr Pro Phe Leu
1               5

<210> SEQ ID NO 148
<211> LENGTH: 7
<212> TYPE: PRT
<213> ORGANISM: Artificial
```

-continued

```
<220> FEATURE:
<223> OTHER INFORMATION: synthetic peptide

<400> SEQUENCE: 148

Ser Ala Asp Ala Ser Pro Gln
1               5

<210> SEQ ID NO 149
<211> LENGTH: 7
<212> TYPE: PRT
<213> ORGANISM: Artificial
<220> FEATURE:
<223> OTHER INFORMATION: synthetic peptide

<400> SEQUENCE: 149

Val Ser Ala His Gln Ala Ser
1               5

<210> SEQ ID NO 150
<211> LENGTH: 4
<212> TYPE: PRT
<213> ORGANISM: Artificial
<220> FEATURE:
<223> OTHER INFORMATION: synthetic peptide

<400> SEQUENCE: 150

Pro Ser Leu Lys
1

<210> SEQ ID NO 151
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(5)
<223> OTHER INFORMATION: X is any amino acid or is absent
<220> FEATURE:
<221> NAME/KEY: MISC_FEATURE
<222> LOCATION: (6)..(6)
<223> OTHER INFORMATION: X is selected from the group consisting of P
      and S
<220> FEATURE:
<221> NAME/KEY: MISC_FEATURE
<222> LOCATION: (9)..(9)
<223> OTHER INFORMATION: X is selected from the group consisting of P,
      S, and T.
<220> FEATURE:
<221> NAME/KEY: MISC_FEATURE
<222> LOCATION: (13)..(17)
<223> OTHER INFORMATION: X is any amino acid or is absent

<400> SEQUENCE: 151

Xaa Xaa Xaa Xaa Xaa Xaa Ser Thr Xaa Pro Pro Ser Xaa Xaa Xaa Xaa
1               5                   10                  15

Xaa

<210> SEQ ID NO 152
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(5)
<223> OTHER INFORMATION: X is any amino acid or is absent.
<220> FEATURE:
<221> NAME/KEY: MISC_FEATURE
```

```
<222> LOCATION: (9)..(9)
<223> OTHER INFORMATION: X is selected from the group consisting of L,
      T, and S.
<220> FEATURE:
<221> NAME/KEY: MISC_FEATURE
<222> LOCATION: (11)..(11)
<223> OTHER INFORMATION: X is selected from the group consisting of A,
      N, P, T, and V.
<220> FEATURE:
<221> NAME/KEY: MISC_FEATURE
<222> LOCATION: (13)..(17)
<223> OTHER INFORMATION: X is any amino acid or is absent.

<400> SEQUENCE: 152

Xaa Xaa Xaa Xaa Xaa Ser Pro Leu Xaa Ser Xaa Pro Xaa Xaa Xaa Xaa
1               5                   10                  15

Xaa
```

IMMUNOSTIMULATORY COMPOSITIONS AND USES THEREOF

CROSS REFERENCE

This application claims the benefit of U.S. Provisional Patent Application No. 60/633,825 filed Dec. 7, 2004, which is hereby incorporated by reference in its entirety.

This application incorporates by reference the contents of a 26.4 kb text file created on Aug. 11, 2010 and named "11663899_sequencelisting.txt," which is the sequence listing for this application.

FIELD OF THE INVENTION

The invention relates to the fields of polypeptides, therapeutics, and immune system activation.

BACKGROUND

Phagocytes such as macrophages and neutrophils provide a primary line of defense against a variety of diseases, including those caused by infectious agents and cancers (Gomme and Bertolini, 2004). During a study of the role of inflammation in development of immunity, Yamamoto and Homma (1991) discovered that a serum protein was required to activate macrophages. This protein is the vitamin D-binding protein (DBP). The human protein is known as group-specific component, or Gc protein. DBP is an abundant, multifunctional, polymorphic glycoprotein in human serum. Highly conserved homologs of this protein occur among all mammalian species (Yang et al., 1990; White and Cooke, 2000). As its name implies, one role of the protein is as a vehicle for circulating vitamin D in blood. Another function involves binding of actin released into the blood during tissue injury. The glycan of the serum protein can be processed to a potent anti-cancer agent, which is expressed through its macrophage activation and anti-angiogenesis activities (Kanda et al., 2002; Gomme and Bertolini, 2004).

DBP is a 458-amino acid protein in humans and consists of three major domains similar to albumin (Head et al., 2002; Otterbein et al., 2002; Verboven et al., 2002). DBP is a glycoprotein that carries a single trisaccharide group (Yang et al., 1985; Cooke and David, 1985). The O-linked glycan is found in the carboxy-terminal Domain III, attached to the hydroxyl group of a specific threonine residue (Thr420 in protein from human). Its structure has been determined as NeuNAc ($\alpha 2 \rightarrow 3$) Gal($\beta 1 \rightarrow 3$) GalNAc($\alpha 1 \rightarrow O$) Thr, with significant amounts of the O-glycan found only on the Gc1 isoform (Coppenhaver et al., 1983; Viau et al., 1983). Some of the glycans contain a second NeuNAc linked $\alpha 2 \rightarrow 6$ to GalNAc. Extensive work by Yamamoto and colleagues (Yamamoto and Kumashiro, 1993; Yamamoto and Naraparaju, 1996 a,b) suggested that DBP has remarkable therapeutic value as an activator of macrophages. Its potent stimulatory activity for macrophage phagocytosis is expressed when its glycosylated site is processed to a single O-linked GalNAc by removal of the NeuNAc (sialic acid) and the Gal residues (Yamamoto and Homma, 1991; Yamamoto and Kumashiro, 1993). The precursor protein can be processed to the active form in vitro by treatment with immobilized sialidase and β-galactosidase (Yamamoto and Kumashiro, 1993; Yamamoto and Naraparaju, 1998). In animals, the modified protein is referred to as DBP-MAF, whereas the active form of the human protein is known as Gc-MAF. These designations are used interchangeably. The active form of the protein reduces tumor cell load (Kisker et al., 2003; Onizuka et al., 2004), provides a therapy against viral infections such as HIV (Yamamoto et al., 1995), and promotes bone growth (Schneider et al., 1995; 2003) and therapy against bone disorders such as ostepetrosis (Yamamoto et al., 1996b). DBP-MAF has also been found to be an effective anti-angiogenesis factor (Kanda et al., 2002; Kisker et al., 2003) and is a potent adjuvant for immunizations (Yamamoto and Naraparaju, 1998). A lectin receptor that specifically binds GalNAc residues was identified on the surface of human macrophages (Iida et al., 1999).

Cancer cells secrete, and some virus particles carry on their surface, an enzymatic activity (N-acetylgalactosaminidase) that depletes the precursor protein in the serum by removing the O-glycoside, which renders the protein inactive as a macrophage activating factor (Yamamoto et al., 1996a, 1997). A decrease in active Gc-MAF may be a major factor in progression of disease. Introduction of the in vitro processed protein leads to dramatic reduction in the amount of cancer cells in animals (Yamamoto and Naraparaju, 1997; Kanda et al., 2002; Kisker et al., 2003; Onizuka et al., 2004) and appears to also reduce the number of HIV particles in infected individuals (Yamamoto et al., 1995). This conclusion is based largely on the decrease in activity of N-acetylgalactosaminidase, whose level appears to be directly correlated with tumor and viral loads in cancer and in HIV-infected patients, respectively (Yamamoto et al., 1997).

SUMMARY OF THE INVENTION

The present invention provides novel immuno-stimulatory polypeptides, and methods for their use and identification. In one aspect, the present invention provides a substantially purified polypeptide comprising an amino acid sequence according to formula 1:

B1-[X1-S-T-X2-P—P—S]—B2 (SEQ ID NO: 151);

wherein X1 is selected from the group consisting of P and S; and

X2 is selected from the group consisting of P, S, and T; and wherein B1 and B2 are independently 1-5 amino acid residues, or are absent.

In a second aspect, the present invention provides a substantially purified polypeptide comprising an amino acid sequence according to formula 2:

B1-[S—P-L-X1-S—X2-P]—B2 (SEQ ID NO: 152);

wherein X1 is selected from the group consisting of L, T, and S; and

X2 is selected from the group consisting of A, N, P, T, and V; and wherein B1 and B2 are independently 1-5 amino acid residues, or are absent.

In a third aspect, the present invention provides a polypeptide comprising an amino acid sequence of a polypeptide according to formula 3:

B1-[X1]-B2;

wherein X is a polypeptide selected from the group consisting of SEQ ID NOS:1-149; and wherein B1 and B2 are independently 1-5 amino acid residues, or are absent.

In a fourth aspect, the present invention provides substantially purified compounds that compete with one or more of the polypeptides according to SEQ ID NOS:1-149 for binding to a GalNAc-specific binding protein, such as GalNAc-specific lectin.

In a fifth aspect, the present invention provides pharmaceutical compositions comprising the substantially purified polypeptides of the invention and a pharmaceutically acceptable carrier.

In further aspects, the present invention provides a purified nucleic acid composition comprising a nucleic acid sequence that encodes a polypeptide according to the invention, expression vectors comprising the purified nucleic acid, and host cells transfected with the expression vectors.

In a further aspect, the present invention provides methods for stimulating immune system activity in a subject, comprising administering to a subject an amount effective of a polypeptide of the invention for stimulating immune system activity.

In a further embodiment, the present invention provides methods for treating a subject with a disorder selected from the group consisting of infections, tumors, bone disorders, immune-suppressed conditions, pain, and angiogenesis-mediated disorders, comprising administering to the subject an amount effective of a polypeptide of the invention.

In a further embodiment, the present invention provides an improved method of vaccination in a subject, comprising administering to a subject receiving a vaccination an amount effective of a polypeptide of the invention for promoting an improved immune system response to the vaccination.

In a further aspect, the present invention provides a method for identifying a GalNAc mimetic compounds, comprising:

a) contacting a plurality of test compounds with a GalNAc-specific lectin under conditions to promote binding of the GalNAc-specific lectin with a GalNAc mimetic compound;

b) removing unbound test compounds;

c) repeating steps (a) and (b) a desired number of times;

d) contacting test compounds bound to the GalNAc-specific lectin with an amount effective of a polypeptide comprising of an amino acid sequence according to SEQ ID NOS:1-149 to displace the bound test compounds if the bound test compounds are acting as GalNAc-mimetics; and e) identifying those test compounds that are displaced from the GalNAc-specific lectin by a polypeptide comprising of an amino acid sequence according to SEQ ID NOS:1-149, wherein such test compounds are GalNAc-mimetic compounds.

BRIEF DESCRIPTION OF THE FIGURES

FIG. 1 is a flowchart describing the algorithm used to search for patterns among the GalNAC mimetic polypeptides.

DETAILED DESCRIPTION OF THE INVENTION

Within this application, unless otherwise stated, the techniques utilized may be found in any of several well-known references such as: *Molecular Cloning: A Laboratory Manual* (Sambrook, et al., 1989. Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., 1990. Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), and *Gene Transfer and Expression Protocols*, pp. 109-128, E. J. Murray, ed. (1991). The Humana Press Inc., Clifton, N.J.).

The single letter designation for amino acids is used predominately herein. As is well known by one of skill in the art, such single letter designations are as follows:

A is alanine; C is cysteine; D is aspartic acid; E is glutamic acid; F is phenylalanine; G is glycine; H is histidine; I is isoleucine; K is lysine; L is leucine; M is methionine; N is asparagine; P is proline; Q is glutamine; R is arginine; S is serine; T is threonine; V is valine; W is tryptophan; and Y is tyrosine.

As used herein, the singular forms "a", "an" and "the" include plural referents unless the context clearly dictates otherwise. For example, reference to a "polypeptide" means one or more polypeptides.

The inventors have identified a series of polypeptide mimetics of GalNAc, using methods described herein. Using similar methods, the inventors previously identified the polypeptide mimetics of GalNAc disclosed in WO05/087793.

Such mimetics act as immunostimulatory compounds and can be used for the various methods of the invention described below. Thus, in a first aspect, the present invention provides a substantially purified polypeptide with an amino acid sequence comprising or consisting of an amino acid sequence according to formula 1:

B1-[X1-S-T-X2-P—P—S]—B2 (SEQ ID NO: 151);

wherein X1 is selected from the group consisting of P and S; and

X2 is selected from the group consisting of P, S, and T; and wherein B1 and B2 are independently 1-5 amino acid residues, or are absent, or functional equivalents thereof.

In various preferred embodiments, X1 is P and X2 is P; X1 is P and X2 is S, X1 is P and X2 is T, X1 is S and X2 is P, X1 is S and X2 is S, or X1 is S and X2 is T.

In a second aspect, the present invention provides a substantially purified polypeptide comprising or consisting of an amino acid sequence according to formula 2:

B1-[S—P-L-X1-S—X2-P]—B2 (SEQ ID NO: 152);

wherein X1 is selected from the group consisting of L, T, and S; and

X2 is selected from the group consisting of A, N, P, T, and V; and wherein B1 and B2 are independently 1-5 amino acid residues, or are absent, or functional equivalents thereof.

In various preferred embodiments, X1 is L and X2 is A; X1 is L and X2 is N; X1 is L and X2 is P; X1 is L and X2 is T; X1 is L and X2 is V; X1 is T and X2 is A; X1 is T and X2 is N; X1 is T and X2 is P; X1 is T and X2 is T; X1 is T and X2 is V; X1 is S and X2 is A; X1 is S and X2 is N; X1 is S and X2 is P; X1 is S and X2 is T; or X1 is S and X2 is V.

In a third aspect, the present invention provides a polypeptide comprising an amino acid sequence of a polypeptide according to formula 3:

B1-[X1]-B2;

wherein X is a polypeptide selected from the group consisting of SEQ ID NOS:1-149; and wherein B1 and B2 are independently 1-5 amino acid residues, or are absent.

Each of the polypeptides according to SEQ ID NOS. 1-149 have been verified as GalNAc mimetics based on their identification in the screening assays described below, and thus can be used as immunostimulatory compounds and for the various methods of the invention described below. Alternatively, X1 can comprise or consist of any of the 2-mers, 3-mers, or 4-mer peptides disclosed herein in Tables 2 and 3.

In each of the first through third aspects of the invention, the B1 and B2 groups are optionally present, for example, to provide appropriate spacing for branched embodiments of the polypeptides, as described below.

In a fourth aspect, the present invention provides substantially purified compounds that compete with one or more of the polypeptides according to SEQ ID NOS:1-149 for binding to a GalNAc-specific binding protein, such as GalNAc-specific lectin.

Such GalNAc-specific lectins include those purified from *Helix pomatia*, *Vicia villosa*, or *Robinia pseudoacacia*, or functional equivalents thereof (commercially available, for example, from Sigma Chemical Co., St. Louis, Mo.). Additional GalNAc-specific lectins include but are not limited to the following: *Bauhinia Purpurea* Lectin (BPL), *Dolichos Biflorus* Lectin (DBA), *Griffonia Simplicifolia* Lectin (GSL I-isolectin B4), *Maculura Pomifera* Lectin (MPL), *Psophocarcpus Tetragonolobus* Lectin (PTL), *Ricinus Communis* Agglutnin (RCA) 1120 and II 60, *Saphora Japonica* Agglutnin (SJA), Soybean Agglutnin (SBA), *Wisteria Floribunda* Agglutinin (WFA). Additional commercial sources of these lectins include the following: Alexis Platform, Reacto Labs, USBiological, Vector Labs, Molecular Probes, Biotrend, Chemikalien GmbH, Invitrogen Corp., Seikaguku America, EY Laboratories, Calbiochem, AlerCheck, Pierce, Accurate Chemical and Scientific Corp., MoBiTec, GALAB, Merck Biosciences, UK, Gentaur France, Biomeda, and Honen Corp, Japan.

The crystal structure of GalNAc-specific lectins from *Robinia pseudoacacia* (Rabijns et al., 2001) and from *Vivia villosa* were published (Babino et al., 2003). These structures are examples of the highly conserved sugar-binding sites of plant lectins (Loris et al., 1998). The critical amino acids in the polypeptide segments that form the carbohydrate-binding site are highly conserved among plant lectins, including those specific for GalNAc or Gal (Osinaga et al., 1997). As an example, the GalNAc-specific binding site in the *Vicia villosa* lectin is formed on the surface of the protein by four loops that contain the amino acids aspartate-85, glycine-103, tyrosine-127, asparagine-129, tryptophan-131 and leucine-213, which interact with functional groups on the sugar (Babino et al., 2003). A conserved aspartate-90 interacts with a divalent cation. Another GalNAc-specific lectin from *Robinia pseudoacacia* (black locust) has a binding site containing similar amino acid residues, e.g., aspartate-87, glycine-104. glycine-105, phenylalanine-129, asparagine-131, isoleucine-216 and aspartate-217 (Rabijns et al., 2001). A lectin that is highly specific for GalNAc, purified from the sea cucumber *Cucumaria echinata* and characterized (Sugawara et al., 2004), contains a similar group of amino acids such as glutamine-101, aspartate-103, tryptophan-105, glutamate-109, arginine-115 and asparagine-123 that interact with the sugar. These amino acids are also found in the GalNAc-binding site of a rat hepatic lectin, RHL-1 (Kolatkar et al., 1998). Various lectins may contain bound divalent cations and are thus designated C-type lectins. A C-type lectin that is particularly important to this invention is a GalNAc-specific lectin on the surface of macrophages and dendritic cells (Suzuki et al., 1996; Iida et al., 1999; Denda-Nagai et al., 2002). (This class of proteins may or may not include specific divalent cations as part of their structure. Any protein, produced by any species or made synthetically, that binds GalNAc in a specific manner is appropriate for use in this technology.

Competition for binding of a polypeptide, of the invention to GalNAc-specific lectins by a test compound can be determined by any suitable technique. For example, the GalNAc-specific lectin can be incubated first with a polypeptide of the invention, and then with the test compound. The test compound competes with the polypeptide of the invention if polypeptide binding to the GalNAc-specific lectin is 90% or less than its binding in the absence of the test compound, more preferably if polypeptide binding to the GalNAc-specific lectin is 80%, 70%, 60%, 50%, 40%, 30%, 20%, or 10% or less than its binding in the absence of the test compound. The desired level of competitive activity of a polypeptide of the invention can be selected for, as will be apparent to those of skill in the art. Similarly, as will be apparent to those of skill in the art, the GalNAc-specific lectin can be incubated first with the test compound, and then with the polypeptide of the invention and competition can be assayed as discussed above. Conditions should be suitable to promote binding, as described in the Examples below. Typically, physiological or near-physiological conditions are suitable for binding of a polypeptide of the invention to GalNAc-specific lectins, for example, room temperature in a buffer solution composed of 50 mM Tris-HCl, pH 7.5, containing 150 mM NaCl, 1 mM $CaCl_2$, 1 mM $MnCl_2$ and 1 mM $MgCl_2$. Polypeptides and the GalNAc-specific lectin can be used in these assays in any amount suitable for the specific assay conducted, preferably between 1 nM and 500 mM; more preferably between 10 nM and 500 mM, even more preferably between 100 nM and 100 mM.

Several variables can be modified to optimize binding to lectins: (1) Detergents are used to reduce nonspecific interactions. Stringency can be increased by increasing the concentration of detergents such as Tween-20, Triton X100, dodecyl maltoside, etc. (2) Temperature can be varied between 4° C. and 55° C. An increase in temperature may cause an increase or decrease in stringency, depending on the specific characteristics of the interaction. (3) The time of the binding step and the elution step can be adjusted to select for differences in the 'on' rates and 'off' rates. Because equilibrium factors apply to the interactions, complex formation can also be altered by concentrations of the reactants such as the target lectin. Displacement of polypeptides from the lectin by addition of test compound is also concentration dependent. These factors can be adjusted to provide optimal results.

The test compounds in this fourth aspect of the invention can comprise small molecules, nucleic acids, or polypeptides, such as those found in various commercially available compound libraries. In a preferred embodiment of this fourth aspect, the test compounds comprise polypeptides.

As used in each of the aspects and embodiments of the invention herein, the term "substantially purified" means that the polypeptides (or nucleic acids) of the invention are substantially free of cellular material, gel materials, culture medium, and contaminating polypeptides or nucleic acids (such as from nucleic acid libraries or expression products therefrom), except as described herein, when produced by recombinant techniques; or substantially free of chemical precursors or other chemicals when chemically synthesized, except as described herein.

As used in each of the aspects and embodiments of the invention herein, the term "polypeptide" is used in its broadest sense to refer to a sequence of subunit amino acids, amino acid analogs, or peptidomimetics. The subunits are linked by peptide bonds, except where noted. The polypeptides described herein may be chemically synthesized or recombinantly expressed, and may be present in a single copy, or in multiple copies (2 or more copies, preferably between 2 and 10; more preferably between 2 and 5 copies). In one non-limiting example, multiple copies of the polypeptide are present in a branched configuration by methods known to those of skill in the art and as disclosed herein, such as *Solid Phase Peptide Synthesis: A Practical Approach* (B. Atherton and R. C. Sheppard, eds., 1989. Oxford University Press, New York, N.Y.); *Solid-Phase Synthesis. A Practical Guide* (S. A. Kates and F. Albericio, eds., 2000. Marcel Dekker, Inc., New York, N.Y.); *Fmoc Solid Phase Peptide Synthesis: A Practical Approach* (W. C. Chan and P. D. White, eds., 2000. Oxford University Press, New York, N.Y.). Technology for synthesis of branched peptides is found in D. N. Posnett, H. McGrath and J. P. Tam (1988) "A novel method for producing anti-peptide antibodies." *Journal of Biological Chemistry* 263: 1719-1725.

The Tn determinant (GalNAc-α-O-Serine/Threonine) is a cryptic antigen that is "covered" on the surface of normal cells but expressed on many human tumor-associated structure (Babino et al., 2003). Lo-Man et al. (1999, 2001, 2004) proposed that antibodies against the Tn antigen should be effective therapeutic tools against cancers. These investigators have shown that clusters of GalNAc at the termini of branched structures elicit strong immunogenic responses. Clusters of the sugar show very different behavior than single residues (Iida et al., 1999; Vichier-Guerre et al., 2000). A synthetic multiple-antigen glycopeptide was shown to be immunogenic in mice and the presence of the antibodies partially protected mice from transplanted tumor cells. The branched molecule with GalNAc residues at the terminus of each branch, or a structure with three GalNAc residues at the terminus of each branch (Lo-Man et al., 2001), are strong antigenic structures, approximately $10^6$-fold more antigenic than a molecule with a single antigen (Lo-Man et al., 1999; Vichier-Guerre et al., 2000). A human macrophage C-type lectin binds GalNAc-containing peptides with high specificity, including the Tn antigen, which is structurally similar to the active site of Gc-MAF. Glycopeptides containing multiple, closely clustered Tn determinants were bound by the lectin with up to 38-fold greater affinity than a single GalNAc attached to the peptide (Suzuki et al., 1996; Iida et al., 1999). The data indicate that the preferred binding of glycopeptides to the human macrophage lectin is as the trimeric protein (Iida et al., 1999), which is similar to observations that monoclonal antibodies recognize clustered GalNAc residues. Thus, clustering of the antigen is required for recognition by antibodies and the clusters are more effective in stimulating macrophages than single Tn molecules. In contrast to the GalNAc-bearing polypeptides, no adverse immunogenic response has been detected thus far to the mimetic polypeptides of this invention.

Where multiple copies of the polypeptides of the invention are present, the multiple copies can be multiple copies of the same polypeptide, or may include two or more different polypeptides, such as a branched multimer incorporating the polypeptide of SEQ ID NO:3 and SEQ ID NO:6, as disclosed below. Those of skill in the art will understand that many such permutations are possible based on the teachings of the present invention.

Preferably, the substantially purified polypeptides of the present invention are chemically synthesized. Synthetic polypeptides, prepared using the well known techniques of solid phase, liquid phase, or peptide condensation techniques, or any combination thereof, can include natural and unnatural amino acids. Amino acids used for peptide synthesis may be standard Boc (N-α-amino protected N-α-t-butyloxycarbonyl)amino acid resin with the standard deprotecting, neutralization, coupling and wash protocols of the original solid phase procedure of Merrifield (1963, J. Am. Chem. Soc. 85:2149-2154), or the base-labile N-α-amino protected 9-fluorenylmethoxycarbonyl (Fmoc) amino acids first described by Carpino and Han (1972, *Journal of Organic Chemistry* 37:3403-3409). Both Fmoc and Boc N-α-amino protected amino acids can be obtained from Sigma-Aldrich, Cambridge Research Biochemical, or other chemical companies familiar to those skilled in the art. In addition, the polypeptides can be synthesized with other N-α-protecting groups that are familiar to those skilled in this art.

Solid phase peptide synthesis may be accomplished by techniques familiar to those in the art and provided, for example, in Stewart and Young (1984) *Solid Phase Synthesis*, Second Edition, Pierce Chemical Co., Rockford, Ill.; Fields and Noble (1990) *International Journal of Peptide and Protein Research* 35:161-214, or using automated synthesizers. The substantially purified polypeptides of the invention may comprise D-amino acids (which are resistant to L-amino acid-specific proteases in vivo), a combination of D- and L-amino acids, and various "designer" amino acids (e.g., β-methyl amino acids, C-α-methyl amino acids, and N-α-methyl amino acids, etc.) to convey special properties. Synthetic amino acids include ornithine for lysine, and norleucine for leucine or isoleucine.

In addition, the substantially purified polypeptides can have peptidomimetic bonds, such as ester bonds, to prepare peptides with novel properties. For example, a peptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a polypeptide would be resistant to protease activity, and would possess an extended half-live in vivo.

The substantially purified polypeptides of the invention may also be present as part of a fusion protein, in which case it may be desirable to synthesize the polypeptide using recombinant DNA technology. Such fusion proteins may include, for example, fusion with peptide transduction domains to permit movement of a fusion protein with the polypeptides of the invention to pass the cell membrane. As used herein, the term "transduction domain" means one or more amino acid sequence or any other molecule that can carry the active domain across cell membranes. These domains can be linked to other polypeptides to direct movement of the linked polypeptide across cell membranes. In some cases the transducing molecules do not need to be covalently linked to the active polypeptide. In a preferred embodiment, the transduction domain is linked to the rest of the polypeptide via peptide bonding. (See, for example, *Cell* 55: 1179-1188, 1988; *Cell* 55: 1189-1193, 1988; *Proc. Natl. Acad. Sci. USA* 91: 664-668, 1994; *Science* 285: 1569-1572, 1999; *J. Biol. Chem.* 276: 3254-3261, 2001; and *Cancer Res* 61: 474-477, 2001).

In another example, the polypeptides of the invention may be present in a fusion protein with full length DBP, or with variations of various c-terminal fragments of DBP, as described in more detail below.

In a further example, the polypeptides of the invention can be fused or otherwise linked to therapeutic agents in order to enhance potential therapeutic effects of both agents. For example, monoclonal antibodies have been generated against a large number of cancers and other pathogenic agents for therapeutic use. Binding of these antibodies to the infectious agent is the first part of the therapy; phagocytosis of the antibody-bound agent by macrophages must occur to eliminate the agent from the body. Therefore, a combination of target-directed antibodies plus the polypeptides of the present invention would be an effective combination therapy. Many other such fusions or linkages to other therapeutic agents will be apparent to those of skill in the art based on the teachings herein.

It will be understood by those of skill in the art that such fusion proteins can comprise the addition of a polypeptide of the invention to the carboxy or amino terminal end of another polypeptide, or can comprise the placement of a polypeptide of the invention within another polypeptide. Those of skill in the art will recognize many such fusion proteins that can be made and used according to the teachings of the present invention.

The substantially purified polypeptides of the invention may be modified by, or combined with, non-polypeptide compounds to produce desirable characteristics, such modifications including but not limited to PEGylation with polyethylene glycol to improve in vivo residency time of the polypeptide, alkylation, phosphorylation, acylation, ester formation, amide formation, lipophilic substituent addition, and modification with markers including but not limited to fluorophores, biotin, dansyl derivatives, and radioactive moieties. Such compounds can be directly linked, or can be linked indirectly, for example via a spacer including but not limited to the B1 and/or B2 groups of general formulas 1-3 of the present invention, β-alanine, gamma-aminobutyric acid (GABA), L/D-glutamic acid, and succinic acid.

In a fifth aspect, the present invention provides pharmaceutical compositions, comprising one or more of the polypeptides disclosed herein, and a pharmaceutically acceptable carrier. Such pharmaceutical compositions are especially useful for carrying out the methods of the invention described below. For administration, the polypeptides are ordinarily combined with one or more adjuvants appropriate for the indicated route of administration. The compounds may be admixed with alum, lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, dextran sulfate, heparin-containing gels, and/or polyvinyl alcohol, and tableted or encapsulated for conventional administration. Alternatively, the compounds of this invention may be dissolved in physiological saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art. The polypeptides may be linked to other compounds to promote an increased half-life in vivo, such as polyethylene glycol. Such linkage can be covalent or non-covalent as is understood by those of skill in the art.

In a sixth aspect, the present invention provides substantially purified nucleic acid sequences encoding the polypeptides of the present invention, or functional equivalents thereof. Appropriate nucleic acid sequences according to this aspect of the invention will be apparent to one of skill in the art based on the disclosure provided herein and the general level of skill in the art. In various preferred embodiments, the nucleic acid sequences comprise or consist of a nucleic acid sequence that encodes the amino acid according to SEQ ID NOS:1-149.

In a seventh aspect, the present invention provides expression vectors comprising DNA control sequences operably linked to the isolated nucleic acid molecules of the present invention, as disclosed above, or functional equivalents thereof. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited to plasmid and viral-based expression vectors.

In an eighth aspect, the present invention provides genetically engineered host cells comprising the expression vectors of the invention, or functional equivalents thereof. Such host cells can be prokaryotic cells or eukaryotic cells, and can be either transiently or stably transfected, or can be transduced with viral vectors. For example, such host cells can be bacterial cells (such as *E. coli*) or algal cells (such as *Chlamydomonas reinhardtii*), which do not generally glycosylate proteins. Thus, in one embodiment, bacterial, plant, or algal cells can be transfected with an expression vector expressing Domain III or full length DBP as a fusion with a polypeptide of the invention, to provide more efficient production of active Domain III or DBP in a non-mammalian system, as described below.

Thus, in a further embodiment of this eighth aspect, the invention provides improved methods for producing active Domain III and DBP analogs, comprising transfecting a bacterial, plant, or algal cell with an expression vector that expresses a fusion protein comprising (a) Domain III or DBP; and (b) a polypeptide according to the present invention, and isolating the fusion protein, wherein the fusion protein is a non-glycosylated but active DBP or Domain III analog. In a preferred embodiment, the fusion protein comprises or consists of a polypeptide of the invention fused to DBP (NP-000574) or with C-terminal fragments of DBP, or functional equivalents thereof. Methods for isolating recombinant proteins from bacterial, plant, and algal cells is well known to those of skill in the art. This preferred embodiment also provides transgenic plants containing the expression vectors of the invention. For transferring the DNA into the plant cells, plant explants may suitably be co-cultivated with *Agrobacterium tumefaciens* or *Agrobacterium rhizogenes*. From the infected plant material (e.g., pieces of leaves, stem segments, roots, protoplasts or suspension-cultivated plant cells), whole plants may then be regenerated in a suitable medium which may contain antibiotics or biozides for the selection of transformed cells. The plants obtained in such a way may then be examined as to whether the introduced DNA is present or not. Other possibilities for introducing foreign DNA, such as using the biolistic method or by transforming protoplasts are known to the skilled person [cf. e.g. Willmitzer, L. (1993) Transgenic plants. In: *Biotechnology, A Multi-Volume Comprehensive Treatise* (H. J. Rehm, G. Reed, A. Puhler, P. Stadler, editors), Vol. 2, 627-659, VCH Weinheim-New York-Basel-Cambridge].

In a ninth aspect, the present invention provides methods for stimulating immune system activity in a subject, comprising administering to a subject an amount effective of a polypeptide according to the invention for stimulating immune system activity.

As used herein the phrase "stimulating immune system activity" means to increase the activity of one or more components of the immune system, including phagocytes, macrophages, and neutrophils. Substances secreted by activated macrophages in turn stimulate other cells of the immune system, in particular dendritic cells. As such, methods for stimulating immune system activity are broadly useful for treating cancer, viral infections, angiogenesis-mediated disorders, bone disorders, immune-suppressed disorders, pain, and as adjuvants for vaccinations.

Thus, in a tenth aspect, the present invention provides methods for treating one or more disorders in a subject, selected from the group consisting of viral infection, cancer, bone disorders, immune suppressed disorder, pain, and angiogenesis-mediated disorders, comprising administering to a subject an amount effective of a polypeptide according to the invention for treating the disorder.

In an eleventh aspect, the present invention provides methods for promoting an improved immune system response to a vaccination, comprising administering to a subject receiving a vaccination an amount effective of a polypeptide according to the invention for promoting an improved immune system response to the vaccination.

In a preferred embodiment of the ninth, tenth, and eleventh aspects of the invention, the subject is a mammal; in a more preferred embodiment, the subject is a human.

In carrying out the methods for promoting an improved immune system response to the vaccination according to the present invention, the polypeptides, or pharmaceutical compositions thereof, of the invention can be administered before, simultaneously with, or after vaccine administration. Where the vaccine is administered on multiple occasions, the polypeptides of the invention can be administered together with a single vaccine administration, or with multiple vaccine administrations. In a preferred embodiment, the polypeptides are administered simultaneously with the one or more rounds of vaccination. Preferred classes of patients include populations at high risk for viral infection, including but not limited to children, health care workers, senior citizens, and those at high risk of specific types of viral infection, such as partners of HIV infected individuals, sex trade workers, and intravenous drug users.

In various embodiments of the ninth, tenth, and eleventh aspects of the invention, administration of the polypeptide is accomplished via direct delivery (for example, by injection), or by gene therapy via administration of an appropriate expression vector of the invention which can be expressed in the target tissue. In embodiments employing gene therapy, it is preferred to use viral expression vectors, including but not limited to adenoviral and retroviral vectors.

In carrying out the methods of the invention, the polypeptides or pharmaceutical compositions thereof may be made up in a solid form (including granules, powders, transdermal or transmucosal patches or suppositories) or in a liquid form (e.g., solutions, suspensions, or emulsions), and may be subjected to conventional pharmaceutical operations such as sterilization and/or may contain conventional adjuvants, such as stabilizers, wetting agents, emulsifiers, preservatives, cosolvents, suspending agents, viscosity enhancing agents, ionic strength and osmolality adjustors and other excipients in addition to buffering agents. Suitable water soluble preservatives which may be employed in the drug delivery vehicle include sodium bisulfite, sodium thiosulfate, ascorbate, benzalkonium chloride, chlorobutanol, thimerosal, phenylmercuric borate, parabens, benzyl alcohol, phenylethanol or antioxidants such as Vitamin E and tocopherol and chelators such as EDTA and EGTA. These agents may be present, generally, in amounts of about 0.001% to about 5% by weight and, preferably, in the amount of about 0.01 to about 2% by weight.

For administration, the polypeptides are ordinarily combined with one or more adjuvants appropriate for the indicated route of administration. The polypeptides may be admixed with alum, lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the polypeptides of this invention may be dissolved in physiological saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

For use herein, the polypeptides may be administered by any suitable route, including local delivery, parentally, transdermally, by inhalation, or topically in dosage unit formulations containing conventional pharmaceutically acceptable carriers, adjuvants, and vehicles. The term parenteral as used herein includes, subcutaneous, intravenous, intramuscular, intrasternal, intratendinous, intraspinal, intracranial, intrathoracic, infusion techniques or intraperitoneally. Suppositories for rectal administration of the active agents in combination with the vaccines can be prepared by mixing the drug with a suitable non-irritating excipient such as cocoa butter and polyethylene glycols which are solid at ordinary temperatures, but liquid at the rectal temperature and will therefore melt in the rectum and release the drug.

Solid dosage forms for oral administration may include capsules, tablets, pills, powders and granules. In such solid dosage forms, the polypeptides may be admixed with at least one inert diluent such as alum, sucrose, lactose or starch. Such dosage forms may also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings. Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents and sweetening, flavoring and perfuming agents.

As used herein for all of the methods of the invention, an "amount effective" of the polypeptides is an amount that is sufficient to provide the intended benefit of treatment. An effective amount of the polypeptides that can be employed ranges generally between about 0.01 µg/kg body weight and about 10 mg/kg body weight, preferably ranging between about 0.05 µg/kg and about 5 mg/kg body weight. However, dosage levels are based on a variety of factors, including the type of disorder, the age, weight, sex, medical condition of the individual, the severity of the condition, the route of administration, and the particular compound employed. Thus, the dosage regimen may vary widely, but can be determined routinely by a physician using standard methods.

Tumors susceptible of treatment by the methods of the invention include lymphomas, sarcomas, melanomas, neuroblastomas, carcinomas, leukemias, and mesotheliomas. Methods of tumor treatment according to the invention can be used in combination with surgery on the subject, wherein surgery includes primary surgery for removing one or more tumors, secondary cytoreductive surgery, and palliative secondary surgery. In a further embodiment, the methods further comprise treating the subject with chemotherapy and/or radiation therapy, which can reduce the chemotherapy and/or radiation dosage necessary to inhibit tumor growth and/or metastasis. As used herein, "radiotherapy" includes but is not limited to the use of radio-labeled compounds targeting tumor cells. Any reduction in chemotherapeutic or radiation dosage benefits the patient by resulting in fewer and decreased side effects relative to standard chemotherapy and/or radiation therapy treatment. In this embodiment, the polypeptide may be administered prior to, at the time of, or shortly after a given round of treatment with chemotherapeutic and/or radiation therapy. In a preferred embodiment, the polypeptide is administered prior to or simultaneously with a given round of chemotherapy and/or radiation therapy. In a most preferred embodiment, the polypeptide is administered prior to or simultaneously with each round of chemotherapy and/or radiation therapy. The exact timing of compound administration will be determined by an attending physician based on a number of factors, but the polypeptide is generally administered between 24 hours before a given round of chemotherapy and/or radiation therapy and simultaneously with a given round of chemotherapy and/or radiation therapy. The tumor treating methods of the invention are appropriate for use with chemotherapy using one or more cytotoxic agent (ie., chemotherapeutic), including, but not limited to, cyclophosphamide, taxol, 5-fluorouracil, adriamycin, cisplatinum, methotrexate, cytosine arabinoside, mitomycin C, prednisone, vindesine, carbaplatinum, and vincristine. The cytotoxic agent can also be an antiviral compound which is capable of destroying proliferating cells. For a general discussion of cytotoxic agents used in chemotherapy, see Sathe, M. et al. (1978) *Cancer Chemotherapeutic Agents Handbook of Clinical Data*, hereby incorporated by reference. When administered as a combination, the therapeutic agents can be formulated as separate compositions that are given at the same time or different times, or the therapeutic agents can be given as a single composition. The methods of the invention are also particularly suitable for those patients in need of repeated or high doses of chemotherapy and/or radiation therapy.

Any infection to which the immune system responds can be treated according to the methods of the invention. Infections, as used herein, are broadly defined to mean situations when the invasion of a host by an agent is associated with the clinical manifestations of infection including, but not limited to, at least one of the following: abnormal temperature, increased heart rate, abnormal respiratory rate, abnormal white blood cell count, fatigue, chills, muscle ache, pain, dizziness, dehydration, vomiting, diarrhea, organ dysfunction, and sepsis. Such infections may be bacterial, viral, parasitic, or fungal in nature. The method may further comprise combinatorial treatment with other anti-infective agents, such as antibiotics. Viruses susceptible to treatment according to the methods of the invention include, but are not limited to adenoviruses, rhinoviruses, rabies, murine leukemia virus, poxviruses, lentiviruses, retroviruses; including disease-causing viruses such as human immunodeficiency virus, hepatitis A and B viruses, herpes simplex virus, cytomegalovirus, human papilloma virus, coxsackie virus, smallpox, hemorrhagic virus, ebola, and human T-cell-leukemia virus. Bacteria susceptible to treatment include, but are not limited to gram negative bacteria and gram-positive bacteria, including but not limited to *Escherichia coli*, *Staphylococcus aureus*, *Staphylococcus epidermidis*, *Streptococcus pneumoniae*, *Mycobacterium tuberculosis*, *Neisseria gonorrhoeae*, *Neisseria meningitis*, *Bordetalla pertussis*, *Salmonella thyhimurium*, *Salmonella choleraesuis*, and *Enterobacter cloacae*, as well as bacterium in the genus *Acinetobacter*, *Actinomyes*, *Bacilus*, *Bordetella*, *Borrelia*, *Brocella*, *Clostridium*, *Corynebacterium*, *Campylobacter*, *Deincoccus*, *Escherichia*, *Enterobacter*, *Enterrococcus*, *Eubacterium*, *Flavobacterium*, *Francisella Glueonobacter*, *Heliobacter*, *Intrasporangium*, *Janthinobacterium*, *Klebsiella*, *Kingella*, *Legionella*, *Leptospira*, *Mycobacterium*, *Moraxella*, *Neisseria*, *Oscillospira*, *Proteus*, *Psendomonas*, *Providencia*, *Rickettsia*, *Salomonella*, *Staphylococcus*, *Shigella*, *Spirilum*, *Streptococcus*, *Treponema*, *Ureplasma*, *Vibrio*, *Wolinella*, *Wolbachia*, *Xanthomonas*, *Yersinis*, and *Zoogloea* Parasitic agents that can be treated by the methods of this aspect of the invention include, but are not limited to *Plasmodium*, *Leishmania*, *Trypanosomes*, *Trichomona*, and including but not limited to parasitic agents in the phylums Acanthocephela, Nematoda, Nemtomorpha, Platyhelminthes, Digena, Eucestoda, Turbellaria, Sarcomastigophora and Protozoa including but not limited to species *Giardia duodenalis*, *Cryptosporidium parvum*, *Cyclospora cayetanenis*, *Toxoplasma gondii*, *Trichinella spiralis*, *Tanenia saginata*, *Taenia solium*, *Wuchereria bancrofti*, *Brugia malay*, *Brugia timori*, *Onchocerca vovulus*, *Loa loa*, *Dracunculus medinensis*, *Mansonella streptocera*, *Mansonella perstans*, *Mansonella ozzardi*, *Schistosoma hematobium*, *Schistosoma mansoni*, *Schistosoma japonicum*, *Ascaris lumbricoides*, *Entrobius vermicularis*, *Trichuris trichiura*, *Ancylostoma brasiliense*, *Ancylostoma duodenale*, *Necator ameicanus*, *Strongyloides stercoralis*, *Capillaria hepatica*, *Angiostrongylus cantonensis*, *Fasciola hepatica*, *Fasciola gigantica*, *Fasciolopsis buski*, *Chlonrchis sinensis*, *Heterophyes heterophyes*, *Paragonimus westermani*, *Diphyllobothrium latum*, *Hymenolepis nana*, *Hymenolepis dimunuta*, *Echinococcus granulosus*, *Dipylidium caninum*, *Entamoeba histolytica*, *Entamoeba coli*, *Entamoeba hartmanni*, *Dientamoeba fragilis*, *Endolimax nana*, *Lodomoeba butschilii*, *Blastocystis hominis*, *Giardia intetinalis*, *Chilomastix menili*, *Blantidium coli*, *Trichomonas vaginalis*, *Leishmania donovani*, *Trypanosoma cruzi*, *Sarcocystis lindemanni*, and *Babesis argentina*. Fungal infections that can be treated by the methods of this aspect of the invention include, but are not limited to fungal meningitis, histoplasmosis, *Candida albicans* infection, as well as *Blastomyces dermatitidis Histotplasma capsulatum*, *Cryptococcus neoformans*, *Sporothrix schenckii*, *Aspergillus fumigatus* and *Pneumocystis carinii* infections.

Angiogenesis-mediated disorders susceptible of treatment by the methods of the invention include solid and blood-borne tumors including but not limited to melanomas, carcinomas, sarcomas, rhabdomyosarcoma, retinoblastoma, Ewing sarcoma, neuroblastoma, osteosarcoma, and leukemia; diabetic retinopathy, rheumatoid arthritis, retinal neovascularization, choroidal neovascularization, macular degeneration, corneal neovascularization, retinopathy of prematurity, corneal graft rejection, neovascular glaucoma, retrolental fibroplasia, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, *Mycobacteria* infections, lipid degeneration, chemical burns, bacterial ulcers, fungal ulcers, Herpes simplex infections, Herpes zoster infections, protozoan infections, Kaposi's sarcoma, Mooren ulcer, Terrien's marginal degeneration, marginal keratolysis, traum, systemic lupus, polyarteritis, Wegeners sarcoidosis, scleritis, Steven's Johnson disease, radial keratotomy, sickle cell anemia, sarcoidosis, pseudoxanthoma elasticum, Pagets disease, vein occlusion, artery occlusion, carotid obstructive disease, chronic uveitis, chronic vitritis, Lyme's disease, Eales disease, Bechets disease, myopia, optic pits, Stargarts disease, pars planitis, chronic retinal detachment, hyperviscosity syndromes, toxoplasmosis, post-laser complications, abnormal proliferation of fibrovascular tissue, hemangiomas, Osler-Weber-Rendu, acquired immune deficiency syndrome, ocular neovascular disease, osteoarthritis, chronic inflammation, Crohn's disease, ulcerative colitis, psoriasis, atherosclerosis, and pemphigoid. (See U.S. Pat. No. 5,712,291)

Bone disorders susceptible of treatment by the methods of the invention include but are not limited to bone fractures, defects, and disorders resulting in weakened bones such as ostepetrosis, osteoarthritis, rheumatoid arthritis, Paget's disease, osteohalisteresis, osteomalacia, periodontal disease, bone loss resulting from multiple myeloma and other forms of cancer, bone loss resulting from side effects of other medical treatment (such as steroids), age-related loss of bone mass and genetic diseases such as osteopetrosis. The polypeptides of the invention can be used alone or together with other compounds to treat bone disorders.

Immune suppressed illnesses or conditions susceptible of treatment by the methods of the invention include but are not limited to severe combined immune deficiency syndrome, acquired immune deficiency syndrome, and at risk populations including but not limited to malnourished individuals and senior citizens. Also susceptible of treatment are diseases such as cancer and viral infections, such as with HIV, in which the pathogenic agent or cell carries or produces an enzyme, N-acetyl-galactosaminidase, that removes GalNAc from Gc-MAF and thus destroys the activity of MAF. An effect of this enzymatic activity is an immuno-suppressed state that can be overcome by treatment with the polypeptides of the invention. Infectious agents may also cause destruction of important cells involved in modifying the precursor Gc protein to the active form Gc-MAF. For example, HIV causes loss of T-lymphocytes, which contain a sialidase that is involved in processing the precursor protein to its active form. Therefore, an immunosuppressed state can be caused by a decrease in processing the Gc-MAF precursor to the active protein and by further removal of the required sugar, which inactivates the protein. The polypeptides of the invention can be used alone or together with other compounds to treat immune suppressed illnesses.

The polypeptides of the invention can also be used as an analgesic to treat pain resulting from any cause, such as an underlying disease or trauma.

In a twelfth aspect, the present invention provides methods for identifying a GalNAc mimetic compound, comprising:

a) contacting a plurality of test compounds with a GalNAc-specific lectin under conditions to promote binding of the GalNAc-specific lectin with a GalNAc mimetic compound;

b) removing unbound test compounds;

c) repeating steps (a) and (b) a desired number of times;

d) contacting test compounds bound to the GalNAc-binding protein with an amount effective of a polypeptide comprising or consisting of an amino acid sequence according to SEQ ID NOS:1-149 to displace the bound test compounds if the bound test compounds are acting as GalNAc-mimetics; and e) identifying those test compounds that are displaced from the GalNAc binding protein by a polypeptide comprising or consisting of an amino acid sequence according to SEQ ID NOS:1-149, wherein such test compounds are GalNAc mimetic compounds.

As used herein the term "contacting" means in vivo or in vitro, preferably in vitro, under suitable conditions for promoting binding of the test polypeptides or compounds to GalNAc-specific lectin. Such techniques are known to those of skill in the art. The assays of the invention can be carried out, for example, as described herein. Modifications of these techniques are well within the level of those of skill in the art with respect to appropriate conditions for contacting as recited above that promote the appropriate binding, as well as techniques for removing unbound polypeptides and identifying the resulting GalNAc-polypeptide mimetics.

As recited in step (c), steps (a) and (b) can be carried out a desired number of additional times, which can be 0 repeats to as many as desirable, preferably between 1 and 5 repeats of step (a) and (b).

Suitable GalNAc-specific lectins for use with the present invention are as described above. The test compounds can be, for example, polypeptides, small molecules, or nucleic acids. In a preferred embodiment, the test compounds are polypeptides.

In a further preferred embodiment of the twelfth aspect, the methods further comprise synthesizing the GalNAc-polypeptide mimetics or test compound mimetics, using methods for synthesis known to those of skill in the art, and as disclosed herein.

In a further aspect, the present invention provides GalNAc mimetic polypeptides or compounds made according to the methods of the twelfth aspect of the invention.

The test compounds (or test polypeptides) of the twelfth aspect can, for example, be from compound libraries, expression libraries, and the like.

The present invention may be better understood with reference to the accompanying examples that are intended for purposes of illustration only and should not be construed to limit the scope of the invention, as defined by the claims appended hereto.

EXAMPLES

Because little more than the sugar and a few amino acids of DBP show phenotypic macrophage activation (Schneider et al., 2003), we designed a polypeptide structure that provides activation but which cannot be inactivated by deglycosylation. Amino acid sequences were identified that would mimic protein-bound GalNAc by screening a phage display library by first selecting phage particles that bind to GalNAc-specific lectins and subsequent elution with free GalNAc. An example of lectins that are useful in the screen is one purified from the snail *Helix pomatia*, which is highly specific for GalNAc (Hammerström and Kabat, 1971) and also binds specifically to the active form of Gc-MAF that contains GalNAc (Kanan et al., 2000). With the lectin as an analog of the receptor on macrophage cells, a polypeptide that binds to the lectin should mimic the structure of Gc-MAF.

The phage display polypeptide libraries were mixed with the *Helix pomatia* lectin conjugated to agarose beads (Sigma-Aldrich Co.). Phage particles that bound to the lectin were recovered by centrifugation, the complexes were washed and bound phage particles were released by a wash with 100 mM GalNAc. The phage were amplified and the 'panning' with the lectin-agarose conjugate was repeated two more times. Panning of the original library was also done with another GalNAc-specific lectin from *Vicia villosa* attached to agarose beads (Sigma-Aldrich Co.). Phage particles that bound to the lectin and were subsequently eluted by competition with free GalNAc were replicated, and the DNA of each was sequenced to derive the amino acid sequences of the variable region.

Table 1 shows amino acid sequences that were derived from the lectin screen. Two phage libraries were used to generate these data, (1) phage with a 7-mer variable region flanked by cysteine residues to allow loop formation by disulfide bond formation ("constrained") and (2) phage particles with a 7-mer variable region ("non-constrained").

TABLE 1

Amino acid sequences derived from DNA sequences of phage particles selected with GalNAc-specific lectins.

7-Mer flanked by C (*H. pomatia* lectin) (Constrained)

| 1. | CNSTTPASC | (SEQ ID NO: 1) |
| 2. | CDPTESSFC | (SEQ ID NO: 2) |
| 3. | CSPHTKDWC | (SEQ ID NO: 3) |
| 4. | CGPDPPRDC | (SEQ ID NO: 4) |
| 5. | CNWHWITNC | (SEQ ID NO: 5) |
| 6. | CSVSQVTTC | (SEQ ID NO: 6) |
| 7. | CEQTLTPQC | (SEQ ID NO: 7) |
| 8. | CLSPLSPVC | (SEQ ID NO: 8) |
| 9. | CLTSSVSTC | (SEQ ID NO: 9) |
| 10. | CVDIPSFQC | (SEQ ID NO: 10) |
| 11. | CTVSGHQDC | (SEQ ID NO: 11) |
| 12. | CLHPMLTDC | (SEQ ID NO: 12) |
| 13. | CCALDLETC | (SEQ ID NO: 13) |
| 14. | CDSPNHRLC | (SEQ ID NO: 14) |
| 15. | CMTSFNLSC | (SEQ ID NO: 15) |

7-Mer flanked by C (VVA Lectin) (Constrained)

| 16. | CLNNSHAEC | (SEQ ID NO: 16) |
| 17. | CPQNTAKAC | (SEQ ID NO: 17) |
| 18. | CPFRSHQRC | (SEQ ID NO: 18) |
| 19. | CPLLPWSPC | (SEQ ID NO: 19) |
| 20. | CSSIPGPSC | (SEQ ID NO: 20) |
| 21. | CVNTSSDSC | (SEQ ID NO: 21) |
| 22. | CPSRTPNHC | (SEQ ID NO: 22) |
| 23. | CYSHNLAEC | (SEQ ID NO: 23) |
| 24. | CTPPKTRTC | (SEQ ID NO: 24) |
| 25. | CDPMRPSMC | (SEQ ID NO: 25) |
| 26. | CPRLSQSPC | (SEQ ID NO: 26) |
| 27. | CSLDYPDSC | (SEQ ID NO: 27) |

7-Mer (*H. pomatia* lectin) (Non-constrained)

| 28. | SHVQCVN | (SEQ ID NO: 28) |
| 29. | IPNPSIR | (SEQ ID NO: 29) |
| 30. | RIRVIRE | (SEQ ID NO: 30) |
| 31. | EYDNSPP | (SEQ ID NO: 31) |
| 32. | RTEHAGF | (SEQ ID NO: 32) |
| 33. | YVSDYDW | (SEQ ID NO: 33) |
| 34. | SDRPSLK | (SEQ ID NO: 34) |
| 35. | YWSPSLK | (SEQ ID NO: 35) |
| 36. | LPLKLLW | (SEQ ID NO: 36) |
| 37. | HAHKVGT | (SEQ ID NO: 37) |
| 38. | ALKPMSH | (SEQ ID NO: 38) |
| 39. | TPDYLAA | (SEQ ID NO: 39) |
| 40. | TPPAAAR | (SEQ ID NO: 40) |
| 41. | YPSTFTR | (SEQ ID NO: 41) |
| 42. | VCRPPCP | (SEQ ID NO: 42) |
| 43. | MPLPFPT | (SEQ ID NO: 43) |
| 44. | ASDTIQT | (SEQ ID NO: 44) |
| 45. | SYYMRDP | (SEQ ID NO: 45) |
| 46. | SQDPSQL | (SEQ ID NO: 46) |
| 47. | LQTFPKP | (SEQ ID NO: 47) |
| 48. | LSNTFGL | (SEQ ID NO: 48) |
| 49. | IPWASLL | (SEQ ID NO: 49) |
| 50. | ITANTLS | (SEQ ID NO: 50) |
| 51. | KISLGGL | (SEQ ID NO: 51) |
| 52. | APQPYRQ | (SEQ ID NO: 52) |
| 53. | HSPADTP | (SEQ ID NO: 53) |
| 54. | TLPALAL | (SEQ ID NO: 54) |
| 55. | NAQKSTL | (SEQ ID NO: 55) |
| 56. | ADEALTL | (SEQ ID NO: 56) |
| 57. | SLSASRI | (SEQ ID NO: 57) |
| 58. | GSASALA | (SEQ ID NO: 58) |
| 59. | SNLSGST | (SEQ ID NO: 59) |
| 60. | QVPVHPS | (SEQ ID NO: 60) |
| 61. | IPGTVHV | (SEQ ID NO: 61) |
| 62. | TTTSFRA | (SEQ ID NO: 62) |

TABLE 1-continued

Amino acid sequences derived from DNA sequences of phage particles selected with GalNAc-specific lectins.

| 63. | ATSLVNL | (SEQ ID NO: 63) |
| 64. | ASGMVFM | (SEQ ID NO: 64) |
| 65. | QLFPCMS | (SEQ ID NO: 65) |
| 66. | LITHPIV | (SEQ ID NO: 66) |
| 67. | YTLGDPS | (SEQ ID NO: 67) |
| 68. | LRPMTVP | (SEQ ID NO: 68) |
| 69. | LGTTPQL | (SEQ ID NO: 69) |
| 70. | TAFLGQH | (SEQ ID NO: 70) |
| 71. | YHQRGPV | (SEQ ID NO: 71) |
| 72. | SHLKSMS | (SEQ ID NO: 72) |
| 73. | HMSRMAN | (SEQ ID NO: 73) |
| 74. | ASTQLLP | (SEQ ID NO: 74) |
| 75. | SALWSPV | (SEQ ID NO: 75) |
| 76. | VLEYSPS | (SEQ ID NO: 76) |
| 77. | SQPATKR | (SEQ ID NO: 77) |

7-Mer (VVA lectin) (Non-constrained)

| 78. | DPKVRTA | (SEQ ID NO: 78) |
| 79. | FERDLPW | (SEQ ID NO: 79) |
| 80. | NRAQNRK | (SEQ ID NO: 80) |
| 81. | AYPFIFR | (SEQ ID NO: 81) |
| 82. | LGILCSR | (SEQ ID NO: 82) |
| 83. | GEYVTLR | (SEQ ID NO: 83) |
| 84. | HLDSSNS | (SEQ ID NO: 84) |
| 85. | LNTARHT | (SEQ ID NO: 85) |
| 86. | TSVLRPG | (SEQ ID NO: 86) |
| 87. | HVPPHAR | (SEQ ID NO: 87) |
| 88. | GPRTHNS | (SEQ ID NO: 88) |
| 89. | QMPAVPS | (SEQ ID NO: 89) |
| 90. | WNPTYPP | (SEQ ID NO: 90) |
| 91. | HQDLRRQ | (SEQ ID NO: 91) |
| 92. | GELPFNP | (SEQ ID NO: 92) |
| 93. | SYLQLPP | (SEQ ID NO: 93) |
| 94. | HVLPVPL | (SEQ ID NO: 94) |
| 95. | ASTYLLG | (SEQ ID NO: 95) |
| 96. | YERAGSH | (SEQ ID NO: 96) |
| 97. | WQPHSHP | (SEQ ID NO: 97) |
| 98. | DSLTPET | (SEQ ID NO: 98) |
| 99. | HPNRFDH | (SEQ ID NO: 99) |
| 100. | NNAILHP | (SEQ ID NO: 100) |
| 101. | RLPGHPS | (SEQ ID NO: 101) |
| 102. | HAPHLWD | (SEQ ID NO: 102) |
| 103. | SPNVPPY | (SEQ ID NO: 103) |
| 104. | IPHLSTL | (SEQ ID NO: 104) |
| 105. | DYPASSF | (SEQ ID NO: 105) |
| 106. | FPRMQPL | (SEQ ID NO: 106) |
| 107. | HNKTSYY | (SEQ ID NO: 107) |
| 108. | THHPIHK | (SEQ ID NO: 108) |
| 109. | TSPLPYW | (SEQ ID NO: 109) |
| 110. | ASPHPAV | (SEQ ID NO: 110) |
| 111. | YSLQHML | (SEQ ID NO: 111) |
| 112. | FPTTYWI | (SEQ ID NO: 112) |
| 113. | CLRAMND | (SEQ ID NO: 113) |
| 114. | NKLPPLF | (SEQ ID NO: 114) |
| 115. | SGLQQPR | (SEQ ID NO: 115) |
| 116. | QATKVRS | (SEQ ID NO: 116) |
| 117. | SPTSARS | (SEQ ID NO: 117) |
| 118. | ASHPSSA | (SEQ ID NO: 118) |
| 119. | QPIGAQR | (SEQ ID NO: 119) |
| 120. | LDTHHLQ | (SEQ ID NO: 120) |
| 121. | QPSLHIS | (SEQ ID NO: 121) |
| 122. | SSFLLGW | (SEQ ID NO: 122) |
| 123. | SQQLASA | (SEQ ID NO: 123) |
| 124. | QPLRAGS | (SEQ ID NO: 124) |
| 125. | EPLRRDT | (SEQ ID NO: 125) |
| 126. | APFLSRL | (SEQ ID NO: 126) |
| 127. | IPHLKLP | (SEQ ID NO: 127) |
| 128. | LPMYSVQ | (SEQ ID NO: 128) |
| 129. | MLPSCAD | (SEQ ID NO: 129) |
| 130. | LLLTSPG | (SEQ ID NO: 130) |
| 131. | SPAGAYY | (SEQ ID NO: 131) |
| 132. | TGPMPAP | (SEQ ID NO: 132) |
| 133. | YKSTLNN | (SEQ ID NO: 133) |
| 134. | SLSVSTR | (SEQ ID NO: 134) |
| 135. | RPLQNNY | (SEQ ID NO: 135) |

TABLE 1-continued

Amino acid sequences derived from DNA sequences
of phage particles selected with GalNAc-
specific lectins.

| | | |
|---|---|---|
| 136. | VVTLSTL | (SEQ ID NO: 136) |
| 137. | HNLHGNL | (SEQ ID NO: 137) |
| 138. | THQCRQC | (SEQ ID NO: 138) |
| 139. | VSPFIRS | (SEQ ID NO: 139) |
| 140. | APRTAFP | (SEQ ID NO: 140) |
| 141. | HGTMTVM | (SEQ ID NO: 141) |
| 142. | NRLAQVH | (SEQ ID NO: 142) |
| 143. | ALLALIP | (SEQ ID NO: 143) |
| 144. | LPYGRQH | (SEQ ID NO: 144) |
| 145. | ARATHPP | (SEQ ID NO: 145) |
| 146. | LQPWVTP | (SEQ ID NO: 146) |
| 147. | RGITPFL | (SEQ ID NO: 147) |
| 148. | SADASPQ | (SEQ ID NO: 148) |
| 149. | VSAHQAS | (SEQ ID NO: 149) |

FIG. 1 shows a flowchart description of the algorithm used to search for patterns among these groups of sequences. The algorithm was developed to determine frequencies of functionally similar dimers, trimers and pentamers, for example. Those that appear most frequently comprise the core of the mimetic. A reduced number of sequences emerge after several rounds of enrichment by the lectin screen.

In order to derive the consensus sequence from the sequences obtained from phage display, a code is written in Java language (1.4.1_02), which is a stand-alone program. The program takes all the sequences that are separated by a separator (|) into a single string as an input. This string is converted into substrings and is stored in a vector, and then these substrings are converted into six-letter codes and transforms into triplets.
Example:
  Actual sequence is AQQSQVY|AQQSQAY
  Converted sequence will be AXXOXUY, AXXOXAY
  Triplets obtained are AXX XXO XOX OXU XUY|AXX XXO XOX OXA XAY Then the program calculates the position, total and frequency of all the triplets and displays in the form of matrix. Total is sum of the individual triplets occurring in all the sequences and Frequency is (Total/Length of the sequence) *100.
Example:

| * | 1 | 2 | 3 | 4 | 5 | TOT | Freq = (TOT/Len) * 100 |
|---|---|---|---|---|---|---|---|
| AXX | 2 | 0 | 0 | 0 | 0 | 2 | 20.0% |
| OXA | 0 | 0 | 0 | 1 | 0 | 1 | 10.0% |
| OXU | 0 | 0 | 0 | 1 | 0 | 1 | 10.0% |
| XAY | 0 | 0 | 0 | 0 | 1 | 1 | 10.0% |
| XOX | 0 | 0 | 2 | 0 | 0 | 2 | 20.0% |
| XUY | 0 | 0 | 0 | 0 | 1 | 1 | 10.0% |
| XXO | 0 | 2 | 0 | 0 | 0 | 2 | 20.0% |

Triplet that occur more than one time are taken and calculated again considering the amino acid immediately before and after the triplet from the sequence.
Example:
Triplets that are occurring more than one time are: AXX, XOX, XXO
Amino acid before and after triplet from the sequence are displayed
Converted: AXXO; Original: AQQS
Converted: AXXO; Original: AQQS
Converted: XXOXU; Original: QQSQV
Converted: XXOXA; Original: QQSQA
Converted: AXXOX; Original: AQQSQ
Converted: AXXOX; Original: AQQSQ
  Results of these pairings were as follows:

TABLE 2

Amino acid pairs (Constrained)

| | |
|---|---|
| 1-mer | A (8, 4.97%), D (5, 3.11%), F (5, 3.11%), H (9, 5.59%), I (6, 3.73%), L (13, 8.07%), N (12. 7.45%), P (26, 16.15%), Q (9, 5.59%), R (7, 4.35%), S (24, 14.91%), T (15, 9.32%), V(5, 3.11%) |
| 2-mer | DP (2, 1.45%), GP (2, 1.45%), HA (2, 1.45%), HQ(2, 1.45%), IT(2, 1.45%), LL(4, 2.9%), LS(3, 2.17%), LS(3, 2.17%), NN(2, 1.45%), NS(3, 2.17%), PF(2, 1.45%), PL(3, 2.17%), PP(3, 2.17%), PQ(2, 1.45%), PS(2, 1.45%), PV(2, 1.45%), QT(2, 1.45%), SH(2, 1.45%), SP(5, 3.62%), SR(2, 1.45%), SS(3, 2.17%), TA(2, 1.45%), TP(3, 2.17%), TT(2, 1.45%) |
| 3-mer | LSP (2, 1.74%), SPL (2, 1.74%) |

TABLE 3

Amino acid pairs (Non-constrained)

| | |
|---|---|
| 1-mer | A (49, 7.45%), C (6, .91%), D (21, 3.19%), E (10, 1.52%), F(18, 2.74%), G(23, 3.5%), H(40, 6.08%), I(20, 3.04%), K(16, 2.43%), L(73, 11.09%), M(14, 2.13%), N(23, 3.5%), P(88, 13.37%), Q(30, 4.56%), R(39, 5.93%), S(75, 11.4%), T(50, 7.6%), V(27, 4.1%), W(11, 167%), Y(25, 3.85%) |
| 2-mer | 'AA'(3, .05%), 'AD'(2.035%), 'AG'(2.035%), 'AL'(6, 1.06%), 'AN'(2.035%), 'AP'(2, 35), 'AQ'(3, .53%), 'AR'(4, .71%), 'AS'(10, 1.77%), 'AT'(3.53%), 'AV'(2.035%), 'DL'(2.03%), 'DP'(4, .71%), 'DS'(2.035%), 'DT'(3, .53%), 'DY'(3, .53%), 'ER'(2.035%), 'FP'(5, .89%), 'FR'(2, .35%), 'GE'(2, .35%), 'GL'(3, .53%), 'GP'(2, .35%), 'GS'(3..53%), 'GT' (3, .53%), 'HA'(4, .71%), 'HH'(2, .35%), 'HK'(2, .35%), 'HL'(5, .89%), 'HM'(2, .35%), 'HN' (2, .35%), 'HP'(9, 1.6%), 'HQ'(2, .35%), 'HS'(2, .35%), 'HV'(4, .71%), 'IL'(2, .35%), 'IP' (4, .71%), 'IR'(3, .53), 'IS'(2, .35%), 'IT'(2, .35%), 'KL'(2, .35%), 'KP'(2, .35%), 'KS'(2.035%), 'KV'(3, .53%), 'LA'(3, .53%), 'LD'(2.035%), 'LF'(2.035%), 'LG'(), 'LH'(2.035%), 'LK'(5, .89%), 'LL'(4, .71%), 'LP'(11, 1.95%), 'LQ'(5, .89%), 'LR'(5, .89%), 'LS'(5, .89%), 'LT'(2.035%), 'LW'(3, .53%), 'MP'(2.035%), 'MS'(4, .71%), 'NA'(2.035%), 'NK' (2.035%), 'NL'(2.035%), 'NP'(3, .53%), 'NR'(3, .53%), 'NS'(3, .53%), 'NT'(3, .53%), 'PA' (7, 1.24%), 'PC'(2.035%), 'PF'(3, .53%), 'PG'(3, .53%), 'PH'(), 'PI'(3, .53%), 'PK'(2, .35%), |

TABLE 3-continued

Amino acid pairs (Non-constrained)

|  |  |
|---|---|
|  | 'PL'(6, 1.06%), 'PM'(2, .35%), 'PN'(3, .53%), 'PP'(8, 1.42%), 'PQ'(2, .35%), 'PR' (3, .53%), 'PS'(12, 2.13%), 'PT'(4, .71%), 'PV'(4, .71%), 'PW'(2, .35%), 'PY'(3, .53%), 'QD' (2, .35%), 'QH'(2, .35%), 'QL'(5, .89%), 'QP'(7, 1.24%), 'RA'(4, .71%), 'RD'(2, .35%), 'RI'(2, .35%), 'RM'(2, .35%), 'RP'(4, .71%), 'RQ'(2, .35%), 'RS'(2, .35%), 'RT'(3, .53%), 'SA'(6, 1.06%), 'SD'(3, .53%), 'SF'(2, .35%), 'SG'(3, .53%), 'SH'(6, 1.06%), 'SL'(9, 1.6%), 'SN'(3, .53%), 'SP'(9, 1.6%), 'SQ'(3, .53%), 'SR'(3, .53%), 'SS'(3, .53%), 'ST'(6, 1.06%), 'SY'(3, .53%), 'TA'(4, .71%), 'TF'(3, .53%), 'TH'(), 'TK'(2, .35%), TL'(7, 1.24%), 'TP' (5, .89%), 'TS'(6, 1.06%), 'TT'(4, .71%), 'TV'(2, .35%), 'TY'(3, .53%), 'VH'(2, .35%), 'VL'(3, .53%), 'VN'(2, .35%), 'VP'(6, 1.06%), 'VR'(2, .35%), 'WS'(2, .35%), 'YD'(2, .35%), 'YL'(3, .53%), 'YP'(4, .71%), 'YS'(2, .35%), 'YV'(2, .3%), 'YW'(3, .53%), 'YY'(2, .35%) |
| 3-mer | 'ALA'(2, .43%), 'AST'(2, .43%), 'ATK'(2, .43%), 'DPS'(2, .43%), 'FPT'(2, .43%), '2,'HPI' (2, .43%), 'HPS'(3, .64%), 'KVR'(2, 0.43%), 'LPF'(2, .43%), 'LPP'(2, .43%), 'LRP'(2, .43%), 'PAV'(2, .43%), 'PHL'(2, .43%), 'PLP'(2, .43%), 'PSL'(3, .64), |
| 4-mer | 'PSLK' (2, 53%) (SEQ ID NO: 150) |

Sequence analysis of DNA of a set of selected phage particles indicate that the method allowed identification of a consensus amino acid sequence, which was then validated against the most frequent pattern identified by the algorithm. The algorithm identified the following consensus sequences:
  Constrained consensus: "P/S, S, T, P/S/T, P, P, S"
  Non-constrained consensus S, P, L, L/T, S, A/N/P/T/V, P The pattern-recognition algorithm disclosed herein is applicable to pattern recognition in any amino acid sequence and does not require an initial query sequence, unlike prior art methods. These pattern recognition techniques can be used to identify any pattern in amino acid sequences, as exemplified herein.

REFERENCES

U.S. Pat. No. 6,410,269
U.S. Patent Application Publication 20030229014
U.S. Patent Application Publication 20040058859
Babino, A., Tello, D., Rojas, A., Bay, S., Osinaga, E. and Alzari, P. M. (2003) The crystal structure of a plant lectin in complex with the Tn antigen. FEBS Lett. 536, 106-110.
Binder, R., Kress, A., Kan, G., Herrmann, K. and Kirschfink, M. (1999) Neutrophil priming by cytokines and vitamin D binding protein (Gc-globulin): impact on C5a-mediated chemotaxis, degranulation and respiratory burst. Molec. Immunol. 36, 885-892.
Cooke, N. E. and David, E. V. (1985) Serum vitamin D-binding protein is a third member of the albumin and alpha fetoprotein gene family. J. Clin. Invest. 76, 2420-2424.
Coppenhaver, D. H., Sollenne, N. P. and Bowman, B. H. (1983) Post-translational heterogeneity of the human vitamin D-binding protein (group-specific component). Arch. Biochem. Biophys. 226, 218-223.
Denda-Nagai, K., Kubota, N., Tsuiji, M., Kamata, M. and Irimura, T. (2002) Macrophage C-type lectin on bone marrow-derived immature dendritic cells is involved in the internalization of glycosylated antigens. Glycobiology 12, 443-450.
Gomme, P. T. and Bertolini, J. (2004) Therapeutic potential of vitamin D-binding protein. Trends Biotechnol. 22, 340-345.
Goochee, C. F., Gramer, M. J., Andersen, D. C., Bahr, J. B. and Rasmussen, J. R. (1991) The oligosaccharides of glycoproteins: bioprocess factors affecting oligosaccharide structures and their effect on glycoprotein properties. Bio/Technology 9, 1347-1355.
Hammarström. S, and Kabat, E. A. (1971) Studies on specificity and binding properties of the blood group A reactive hemagglutinin from *Helix pomatia*. Biochemistry 10, 1684-1692.

Head, J. F., Swamy, N. and Ray, R. (2002) Crystal structure of the complex between actin and human vitamin D-binding protein at 2.5 A resolution. Biochemistry 41, 9015-9020.
Iida, S., Yamamoto, K. and Irimura, T. (1999) Interaction of human macrophage C-type lectin with O-linked N-acetylgalactosamine residues on mucin glycopeptides. J. Biol. Chem. 274, 10697-10705.
Ischiropoulos, H., Zhu, L and Beckman, J. S. (1992) Peroxynitrite formation from macrophage-derived nitric oxide. Arch. Biochem. Biophys. 298, 446-451.
Johnston, R. B., Godzik, C. A. and Cohn, Z. A. (1978) Increased superoxide anion produced by immunologically activated and chemically elicited macrophages. J. Exp. Med. 148, 115-126.
Kanan, R. M., Cook, D. B. and Datta, H. K. (2000) Lectin immunoassay for macrophage activating factor (Gc-MAF) produced by deglycosylation of Gc-globulin: evidence for noninducible generation of Gc-MAF. Clin. Chem., 46, 412-414.
Kanda S., Mochizuki, Y., Miyata, Y., Kanetake, H. and Yamamoto, N. (2002) Effects of vitamin $D_3$-binding protein-derived macrophage activating factor (GcMAF) on angiogenesis. J. Natl. Cancer Inst. 94, 1311-1319.
Kisker, O., Onizuka, S., Becker, C. M., Fannon, M., Flynn, E., D'Amato, R., Zetter, B., Folkman, J., Ray, R., Swamy, N., and Pirie-Sheperd, S. (2003) Vitamin D binding protein-macrophage activating factor (DBP-maf) inhibits angiogenesis and tumor growth in mice. Neoplasia 5, 32-40.
Kolatkar, A. R., Leung, A. K., Isecke, R., Brossmer, R., Drickamer, K. and Weis, W. L. (1998) Mechanism of N-acetylgalactosamine binding to a C-type animal lectin carbohydrate-recognition domain. J. Biol. Chem. 273, 19502-19508.
Lo-Man, R., Bay, S., Vichier-Guerre, S., Dériaud, E., Cantacuzène, D. and Leclerc, C. (1999) A fully synthetic immunogen carrying a carcinoma-associated carbohydrate for active specific immunotherapy. Cancer Res. 59, 1520-1524.
Lo-Man, R., Vichier-Guerre, S., Bay, S., Dériaud, E., Cantacuzème, D. and Leclerc, C. (2001) Anti-tumor immunity provided by a synthetic multiple antigenic glycopeptide displaying a tri-Tn glycotope. J. Immunol. 166, 2849-2854.
Lo-Man, R., Vichier-Guerre, S., Perraut, R., Dériaud, E., Huteau, V., BenMohamed, L., Diop, O. M., Livingston, P. O., Bay, S, and Leclerc, C. (2004) A fully synthetic therapeutic vaccine candidate targeting carcinoma-associated Tn carbohydrate antigen induces tumor-specific antibodies in nonhuman primates. Cancer Res. 64, 4987-4994.

Loris, R., Hamelryck, T, Bouckaert, J. and Wyns, L. (1998) Legume lectin structure. Biochim. Biophys. Acta 1383, 9-36.

Marklund, S. and Marklund, G. (1974) Involvement of superoxide anion radical in the auto-oxidation of pyrogallol and a convenient assay of superoxide dismutase. Eur. J. Biochem. 47, 469-474.

Onizuka, S., Kawakami, S., Taniguchi, K, Fujioka, H. and Miyashita, K. (2004) Pancreatic carcinogenesis: apoptosis and angiogenesis. Pancreas 28, 317-319.

Osinaga, E., Tello, D., Batthyany, C., Bianchet, M., Tavares, G., Durán, R., Cerveñansky, C., Camoin, L., Roseto, A. and Alzari, P. M. (1997) Amino acid sequences and three-dimensional structure of the Tn-specific isolectin B4 from *Vicia villosa*. FEBS Lett. 412, 190-196.

Otterbein, L. R., Cosio, C., Graceffa, P. and Dominguez, R. (2002) Crystal structure of the vitamin D-binding protein and its complex with actin: structural basis of the actin-scavenger system. Proc. Natl. Acad. Sci. USA 99, 8003-8008.

Pick, E. and Mizel, D. (1981) Rapid microassays for the measurement of superoxide and hydrogen peroxide production by macrophages in culture using an automatic enzyme immunoassay reader. J. Immunol. Meth. 46, 211-226.

Rabijns, A., Verboven, C., Rougé, P., Barre, A., Van Damme, E. J. M., Peumans, W. J., De Ranter, C. J. (2001) Structure of a legume lectin from the bark of *Robinia pseudoacacia* and its complex with N-acetylgalactosamine. Proteins 44, 470-478.

Schneider, G., Benis, K., Flay, N., Ireland, R. and Popoff, S. (1995) Effects of vitamin D-binding protein-macrophage activating factor (DBP-MAF) infusion on bone resorption in two osteopetrotic mutations. Bone 16, 657-662.

Schneider, G. B., Greccio, K. J., Safadi, F. F. and Popoff, S. N. (2003) The anabolic effects of vitamin D-binding protein-macrophage activating factor (DBP-MAF) and a novel small polypeptide on bone. Critical Rev. Eukaryotic Gene Exp. 13, 277-284.

Sugawara, H., Kusunoki, M., Kurisu, G., Fujimoto, T., Aoyagi, H. and Hatakeyama, T. (2004) Characteristic recognition of N-acetylgalactosamine by an invertebrate C-type lectin, CEL-I, revealed by X-ray crystallographic analysis. J. Biol. Chem. 279, 45219-45225.

Suuzki, N., Yamamoto, K., Toyoshima, S., Osawa, T. and Irimura, T. (1996) Molecular cloning and expression of cDNA encoding human macrophage C-type lectin: It's unique carbohydrate binding specificity for Tn antigen. J. Immunol. 156, 128-135.

Verboven, C., Rabijns, A., De Maeyer, M., Van Baeten, H., Bouillon, R. and De Ranter, C. (2002) A structural basis for the unique binding features of the human vitamin D-binding protein. Nature Struct. Biol. 9, 131-136.

Viau, M., Constans, H., Debray, H. and Montreuil, J. (1983) Isolation and characterization of the o-glycan chain of the human vitamin D-binding protein. Biochem. Biophys. Res. Commun. 117, 324-331.

Vichier-Guerre, S., Lo-Man, R., Bay, S., Deriaud, E., Nakada, H, Leclerc, C. and Cantacuzène, D. (2000) Short synthetic glycopeptides successfully induce antibody responses to carcinoma-associated Tn antigen. J. Peptide Res. 55, 173-180.

Wan, C. P., Park, C. S, and Lau, B. H. S. (1993) A rapid and simple microfluorometric phagocytosis assay. J. Immunol. Meth. 162, 1-7.

White, P. and Cooke, N. (2000) The multifunctional properties and characteristics of vitamin D-binding protein. Trends Endocrin. Metabol. 11, 320-327.

Yamamoto, N. and Homma, S. (1991) Vitamin $D_3$ binding protein (group-specific component) is a precursor for the macrophage-activating signal factor from lysophosphatidylcholine-treated lymphocytes. Proc. Natl. Acad. Sci. USA 88, 8539-8543.

Yamamoto, N. and Kumashiro, R. (1993) Conversion of vitamin $D_3$-binding protein (group-specific component) to a macrophage-activating factor by the stepwise action of β-galactosidase of B cells and sialidase of T cells. J. Immunol. 151, 2794-2802.

Yamamoto, N. and Naraparaju V. R. (1996a) Vitamin $D_3$-binding protein as a precursor for macrophage activating factor in the inflammation-primed macrophage activation cascade in rats. Cell. Immunol. 170, 161-167.

Yamamoto, N. and Naraparaju, V. R. (1996b) Role of vitamin $D_3$-binding protein in activation of mouse macrophages. J. Immunol. 157, 1744-1749.

Yamamoto, N. and Naraparaju, V. R. (1997) Immunotherapy of BALB/c mice bearing Ehrlich ascites tumor with vitamin C-binding protein-derived macrophage activating factor. Cancer Res. 57, 2187-2193.

Yamamoto, N. and Naraparaju, V. R. (1998) Structurally well-defined macrophage activating factor derived from vitamin $D_3$-binding protein has a potent adjuvant activity for immunization. Immunol. Cell Biol. 76, 237-244.

Yamamoto, N., Naraparaju, V. R. and Asbell, S. O. (1996) Deglycosylation of serum vitamin $D_3$-binding protein leads to immunosuppression in cancer patients. Cancer Res. 56, 2827-2831.

Yamamoto, N., Naraparaju, V. and Orchard, P. J. (1996) Defective lymphocyte glycosidases in the macrophage activation cascade of juvenile osteopetrosis. Blood 88, 1473-1478.

Yamamoto, N., Naraparaju, V. R and Srinivasula, S. M. (1995) Structural modification of serum vitamin $D_3$-binding protein and immunosuppression in AIDS patients. AIDS Res. Human Retrovir. 11, 1373-1378.

Yamamoto, N., Naraparaju, V. R and Urade, M. (1997) Prognostic utility of serum α-N-acetylgalactosaminidase and immunosuppression resulted from deglycosylation of serum Gc protein in oral cancer patients. Cancer Res. 57, 295-299.

Yang, F., Bergeron, J. M., Linehan, L. A., Lalley, P. A., Sakaguchi, A. L. and Bowman, B. H. (1990) Mapping and conservation of the group-specific component gene in mouse. Genomics 7, 509-516.

Yang, F., Brune, J. L., Maylor, S. L., Cupples, R. L., Naberhaus, K. H. and Bowman, B. H. (1985) Human group-specific component (Gc) is a member of the albumin family. Proc. Natl. Acad. Sci. USA 82, 7994-7998.

We claim:

1. A substantially purified polypeptide comprising the amino acid sequence according to formula 2:

B1-[S—P-L-X1-S—X2-P]—B2 (SEQ ID NO: 152);

wherein X1 is selected from the group consisting of L, T, and S; and

X2 is selected from the group consisting of N, P, T, and V; and wherein B1 and B2 are independently 1-5 amino acid residues, or are absent.

2. A pharmaceutical composition comprising the substantially purified polypeptide of claim 1 and a pharmaceutically acceptable carrier.

3. The substantially purified polypeptide of claim 1, wherein X1 is L.

4. The substantially purified polypeptide of claim 1, wherein X2 is N.

5. The substantially purified polypeptide of claim 1, wherein X1 is L and X2 is N.

6. The substantially purified polypeptide of claim 1, wherein B1 and B2 are absent.

7. The substantially purified polypeptide of claim 5, wherein B1 and B2 are absent.

8. A substantially purified polypeptide consisting of the amino acid sequence according to formula 2:

B1-[S—P-L-X1-S—X2-P]-B2 (SEQ ID NO: 152);

wherein X1 is selected from the group consisting of L, T, and S; and

X2 is selected from the group consisting of A, N, P, T, and V; and wherein B1 and B2 are independently 1-5 amino acid residues, or are absent.

9. The substantially purified polypeptide of claim 8, wherein X1 is L.

10. The substantially purified polypeptide of claim 8, wherein X2 is N.

11. The substantially purified polypeptide of claim 8, wherein X1 is L and X2 is N.

12. The substantially purified polypeptide of claim 8, wherein B1 and B2 are absent.

13. The substantially purified polypeptide of claim 11, wherein B1 and B2 are absent.

* * * * *